US008574874B2

(12) United States Patent
Ju et al.

(10) Patent No.: US 8,574,874 B2
(45) Date of Patent: Nov. 5, 2013

(54) MICROORGANISMS FOR PRODUCING L-AMINO ACIDS AND PROCESS FOR PRODUCING L-AMINO ACIDS USING THEM

(75) Inventors: Jae Yeong Ju, Gyeonggi-do (KR); Kwang Ho Lee, Daejeon (KR); Hyun Ae Bae, Seoul (KR); Hyo Jin Kim, Seoul (KR); Keun Chul Lee, Gyeonggi-do (KR); Young Bin Hwang, Seoul (KR); Kyu Soo Cho, Seoul (KR); Hye Min Park, Gyeongsangnam-do (KR); Hyun Ah Kim, Jeollabuk-do (KR)

(73) Assignee: CJ Cheiljedang Corporation, Seoul (KR)

(*) Notice: Subject to any disclaimer, the term of this patent is extended or adjusted under 35 U.S.C. 154(b) by 0 days.

(21) Appl. No.: 12/743,675

(22) PCT Filed: Feb. 11, 2010

(86) PCT No.: PCT/KR2010/000872
§ 371 (c)(1),
(2), (4) Date: Dec. 21, 2010

(87) PCT Pub. No.: WO2010/093182
PCT Pub. Date: Aug. 19, 2010

(65) Prior Publication Data
US 2011/0111466 A1    May 12, 2011

(30) Foreign Application Priority Data

Feb. 13, 2009 (KR) .................. 10-2009-0012048

(51) Int. Cl.
*C12P 13/22* (2006.01)
(52) U.S. Cl.
USPC ........................................ 435/108
(58) Field of Classification Search
USPC ........................................ 435/108
See application file for complete search history.

(56) References Cited

U.S. PATENT DOCUMENTS

| 4,806,480 | A | 2/1989 | Lopez | |
|---|---|---|---|---|
| 6,960,455 | B2 * | 11/2005 | Livshits et al. | 435/106 |
| 7,179,623 | B2 | 2/2007 | Livshits et al. | |

FOREIGN PATENT DOCUMENTS

| KR | 10-2008-0059604 | 6/2008 |
|---|---|---|
| WO | WO 2006/121755 A2 | 11/2006 |

OTHER PUBLICATIONS

Written Opinion Oct. 14, 2010.*
Alterthum, F. and Ingram, L.O., "Efficient ethanol production from glucose, lactose, and xylose by recombinant *Escherichia coli*," *Appl. Environ. Microbiol.* 55(8):1943-48, American Society for Microbiology, United States (1989).
Bockmann, J., et al., "Characterization of a chromosomally encoded, non-PTS metabolic pathway for sucrose utilization in *Escherichia coli* EC3132.," *Mol. Gen. Genet.* 235(1):22-32, Springer-Verlag, Germany (1992).
Bogs, J. and Geider, K., "Molecular Analysis of Sucrose Metabolism of *Erwinia amylovora* and Influence on Bacterial Virulence," *J. Bacteriol.* 182(19):5351-58, American Society for Microbiology, United States (2000).
Bradford, M.M., "A Rapid and Sensitive Method for the Quantitation of Microgram Quantities of Protein Utilizing the Principle of Protein-Dye Binding," *Anal. Biochem.* 72:248-54, Academic Press, United States (1976).
Burgard, A.P. and Maranas, C.D., "Probing the Performance Limits of the *Escherichia coli* Metabolic Network Subject to Gene Additions or Deletions," *Biotechnol. Bioeng.* 74(5):364-75, John Wiley & Sons, Inc., United States (2001).
Copeland, L., et al., "Fructokinase (Fraction III) of Pea Seeds," *Plant Physiol.* 62:291-94, American Society of Plant Biologists, United States (1978).
Cowan, P.J., et al., "Characterization of the Major Promotor for the Plasmid-Encoded Sucrose Genes *scrY, scrA*, and *scrB*," *J. Bacteriol.* 173(23):7464-70, American Society for Microbiology, United States (1991).
Datsenko, K.A. and Wanner, B.L., "One-step inactivation of chromosomal genes in *Escherichia coli* K-12 using PCR products," *Proc. Nat. Acad. Sci.* 97(12):6640-45, National Academy of Sciences, United States (2000).
DiRusso, C.C. and Nyström, T., "The fats of *Escherichia coli* during infancy and old age: regulation by global regulators, alarmones and lipid intermediates," *Mol. Microbiol.* 27(l):1-8, Blackwell Science Ltd., England (1998).
Flores, S., et al., "Analysis of Carbon Metabolism in *Escherichia coli* Strains with an Inactive Phosphotransferase System by $^{13}C$ Labeling and NMR Spectroscopy," *Metab. Eng.* 4:124-37, Elsevier Science (2002).
Flores, N., et al., "Adaptation for fast growth on glucose by differential expression of central carbon metabolism and *gal* regulon genes in an *Escherichia coli* strain lacking the phosphoenolpyruvate: carbohydrate phosphotransferase system," *Metab. Eng.* 7:70-87, Elsevier Inc., Belgium (2005).
Gosset, G., "Improvement of *Escherichia coli* production strains by modification of the phosphoenolpyruvate:sugar phosphotransferase system," *Microb. Cell Fact.* 4:14, 11 pages, BioMed Central Ltd., England (2005).
Hernández-Montalvo, V., et al., "Characterization of sugar mixtures utilization by an *Escherichia coli* mutant devoid of the phosphotransferase system," *Appl. Microbiol. Biotechnol.* 57:186-91, Springer-Verlag, Germany (2001).
Jahreis, K., et al., "Adaptation of Sucrose Metabolism in the *Escherichia coli* Wild-Type Strain EC3132," *J. Bacteriol.* 184(19):5307-16, American Society for Microbiology, United States (2002).
Kornberg, H.L., "Routes for fructose utilization by *Escherichia coli*," *J. Mol. Microbiol. Biotechnol.* 3(3):355-59, Karger, Switzerland (2001).

(Continued)

*Primary Examiner* — Tekchand Saidha
(74) *Attorney, Agent, or Firm* — Sterne, Kessler, Goldstein & Fox P.L.L.C.

(57) ABSTRACT

The present invention relates to a transformed microorganism producing an L-amino acid using sucrose as a main carbon source, and a method for producing an L-amino acid using the same.

14 Claims, 2 Drawing Sheets

(56) References Cited

OTHER PUBLICATIONS

Figure 1:
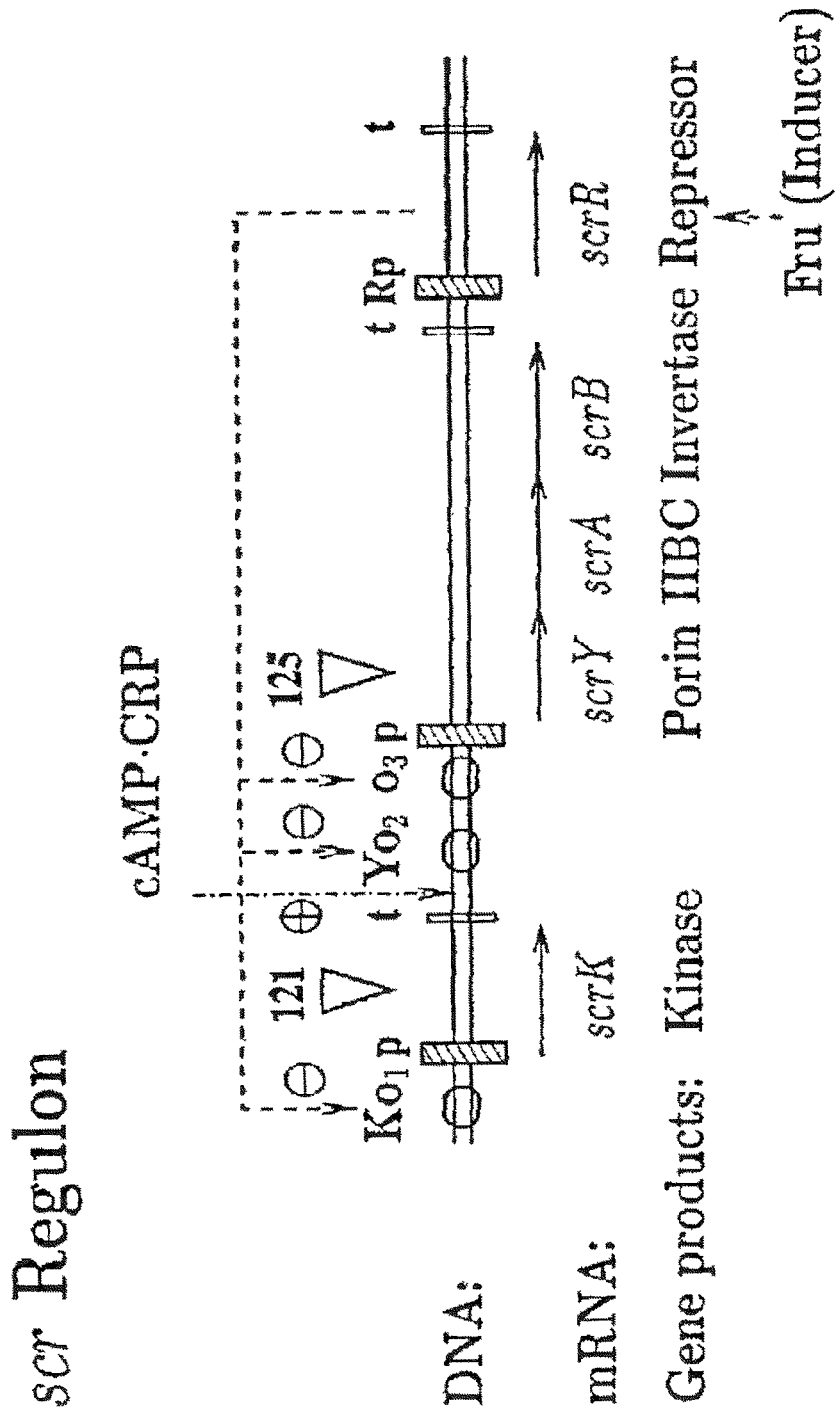

Miller, B.G. and Taines, R.T., "Reconstitution of a Defunct Glycolytic Pathway via Recruitment of Ambiguous Sugar Kinases," *Biochem.* 44:10776-83, American Chemical Society (2005).

Olson, M.M., et al., "Production of tyrosine from sucrose or glucose achieved by rapid genetic changes to phenylalanine-producing *Escherichia coli* strains," *Appl. Microbiol. Biotechnol.* 74:1031-40, Springer-Verlag, Germany (2007).

Reid, S.J., and Abratt, V.R., "Sucrose utilisation in bacteria: genetic organisation and regulation," *Appl. Microbiol Biotechnol.* 67:312-21, Springer-Verlag, Germany (2005).

Sahin-Tóth, M., et al., "Active Transport by The CscB Permease in *Escherichia coli* K-12," *Biochem. Biophys. Res. Commun.* 208(3):1116-23, Academic Press, United States (1995).

Sahin-Tóth, M., et al., "Cloning, sequencing, and expression of cscA invertase from *Escherichia coli* B-62," *Can. J. Microbiol.* 45:418-22, NRC Research Press, Canada (1999).

Sato, Y., et al., "Characterization and Sequence Analysis of the *scrA* Gene Encoding Enzyme $II^{Scr}$ of the *Streptococcus mutans* Phosphoenolpyruvate-Dependent Sucrose Phosphotransferase System," *J. Bacteriol.* 171(1):263-71, American Society for Microbiology, United States (1989).

Schmid, K., et al., "Plasmid-Mediated Uptake and Metabolism of Sucrose by *Escherichia coli* K-12.," *J. Bacteriol.* 151(1):68-76, American Society for Microbiology, United States (1982).

Shukla, V.B., et al., "Production of D(••••••)-lactate from sucrose and molasses," *Biotechnol. Lett.* 26:689-93, Kluwer Academic Publishers, Netherlands (2004).

Sprenger, G.A. and Lengeler, J.W., "Analysis of Sucrose Catabolism in *Klebsiella pneumoniae* and in $Scr^+$ Derivatives of *Escherichia coli* K12," *J. Gen. Microbiol.*, 134:1635-44, Society for General Microbiology, England (1988).

Tsunekawa, H., et al., "Acquisition of a Sucrose Utilization System in *Escherichia coli* K-12 Derivatives and Its Application to Industry," *Appl. Environ. Microbiol.* 58(6):2081-88, American Society for Microbiology, United States (1992).

Wang, B. and Kuramitsu, K., "Control of Enzyme $II^{scr}$ and Sucrose-6-Phosphate Hydrolase Activities in *Streptococcus mutans* by Transcriptional Repressor ScrR Binding to the *cis*-Active Determinants of the *scr* Regulon," *J. Bacteriol.* 185(19):5791-99, American Society for Microbiology, United States (2003).

"*Escherichia coli* anion symport for sucrose (cscB), fructokinase (cscK), and sucrose hydrolase (cscA) genes, complete cds; and regulatory protein (cscR') gene, partial cds," NCBI Entrez GenBank Report, Accession No. AY314757.1, Shukla, V.B., Entry Date Jul. 2003.

"*Escherichia coli* vacJ gene, yfdC gene, cscB gene, cscK gene, cscA gene, cscR gene, dsDX gene, tRNA-Arg gene and partial b2345 gene, strain EC3132," NCBI Entrez, GenBank Report, Accession No. X81461.2, Jahreis, K., Entry Date Apr. 2005.

International Search Report for International Application No. PCT/KR2010/000872, Korean Intellectual Property Office, Republic of Korea, mailed Oct. 14, 2010.

International Preliminary Report on Patentability, including the Written Opinion of the International Searching Authority, for International Application No. PCT/KR2010/000872, The International Bureau of WIPO, Geneva, Switzerland, issued Sep. 13, 2011.

English language abstract of Korean Patent Publication No. KR 10-2008-0059604 A, (2008).

\* cited by examiner

MICROORGANISMS FOR PRODUCING L-AMINO ACIDS AND PROCESS FOR PRODUCING L-AMINO ACIDS USING THEM

REFERENCE TO SEQUENCE LISTING SUBMITTED ELECTRONICALLY VIA EFS-WEB

The content of the electronically submitted sequence listing (Name: SequenceListing.txt Size: 47,574 bytes; and Date of Creation: Apr. 29, 2010) filed herewith is incorporated herein by reference in its entirety.

BACKGROUND OF THE INVENTION

1. Field of the Invention

The present invention relates to a transformed microorganism producing an L-amino acid with a high yield using sucrose as a main carbon source, and a method for producing an L-amino acid using the same.

2. Background Art

Due to growing demand for bio-fuel production and crop failures caused by unusual climate, the price of starch sugar used as a fermentation feedstock has rapidly increased. Alternatively, the use of sucrose or molasses containing a high concentration of sucrose, cheaper than starch sugar, as a carbon source in industrial fermentation, is advantageous to ensure the cost competitiveness. Approximately 50% of the E. coli isolated from nature is able to metabolize sucrose, but E. coli K12 strain, B strain and C strain usually used in industrial fermentation, have no ability to assimilate sucrose (Mol. Microbiol. (1998) 2:1-8, Can. J. Microbiol. (1999) 45:418-422). Therefore, among the most important challenges in the fermentation industry is the investigation of genes involved in sucrose assimilation, the establishment of enhanced sucrose assimilation-related genes by improvement, and the application of the genes to the sucrose non-assimilative, industrial E. coli strains for the production of desired metabolites.

To impart sucrose-assimilating ability to industrial E. coli strains, methods of introducing a sucrose assimilation gene or gene cluster derived from microorganisms having a sucrose-assimilating ability have been generally used. For example, a method of imparting sucrose-assimilating ability to E. coli K12 by transformation with the scr regulon present in the species Salmonella belonging to the family Enterobacteriaceae (J. Bacteriol. (1982) 151:68-76, Mol. Microbiol. (1998) 2:1-8, J. Bacteriol. (1991) 173:7464-7470, U.S. Pat. No. 7,179,623), Klebsiella pneumoniae (J. Gen. Microbiol. (1988) 134:1635-1644), Erwinia amylovora (J. Bacteriol. (2000) 182:5351-5358) has been well known in the art. Introduction of the csc regulon derived from non-K12 E. coli having the sucrose-assimilating ability or pathogenic E. coli (Appl. Environ. Microbiol. (1992) 58:2081-2088, U.S. Pat. No. 6,960,455), introduction of sucrose assimilation gene that is present in conjugative plasmid scr53 isolated from E. coli AB1281 (U.S. Pat. No. 4,806,480), and introduction of scr regulon and sac operon derived from Gram-positive microorganisms, Streptococcus mutans (J. Bacteriol. (1989) 171:263-271) and Bacillus subtilis (J. Bacteriol. (1989) 171: 1519-1523) are also known.

Conventionally, L-amino acid has been industrially produced by fermentation methods using microorganism strains isolated from nature or artificial mutants of said bacterial strains, which have been modified in such a way that the L-amino acid production yield is enhanced. Many techniques to enhance L-amino acid production yields have been reported. For example, techniques for enhancing production yields include increasing the activities of enzymes involved in amino acid biosynthesis or desensitizing the target enzymes of the feedback inhibition by the resulting L-amino acid. Meanwhile, amino acid production yields of L-amino acid-producing strains can be improved by enhancing L-amino acid excretion activity. For example, bacteria belonging to the genus corynebacterium in which expression of an L-lysine secretion gene is increased have been used. In addition, expression of genes coding for the efflux proteins which act to enhance secretion of L-cysteine, L-cystine, N-acetylserine, or thiazolidine derivatives is regulated to increase L-amino acid production activity.

The sucrose utilization system is largely divided into the Scr-PTS system and the Scr-non PTS system. Most microorganisms capable of utilizing sucrose have the Scr-PTS (phosphoenolpyruvate dependent sucrose phosphotransferase) system. The Scr-PTS system allows efficient uptake of a low level of sucrose, but the sucrose uptake process requires PEP (phosphoenolpyruvate) consumption to reduce the intracellular PEP pool. The Scr-non PTS system is a system using proton symport-type sucrose permease, exemplified by the well known csc gene clusters containing cscB coding for sucrose permease. csc regulon consists of cscB (sucrose permease or proton symport-type sucrose permease), cscK (fructokinase), cscA (sucrose hydrolase), and cscR (sucrose transcriptional regulator), and is negatively controlled by two operons, cscKB and cscR (Jahreis K et al., J. Bacteriol. (2002) 184:5307-5316).

PEP is a key metabolite in the central metabolic pathway, and functions as a phosphate donor of the sugar PTS system. PEP is also involved in ATP synthesis catalyzed by pyruvate kinase, and functions as a direct precursor of several amino acids or oxaloacetate (OAA) (Metab. Eng. (2002) 4:124-137, Microb. Cell Fact. (2005) 4:14). In particular, OAA is used as a carbon skeleton of amino acids such as threonine, isoleucine, methionine, lysine, asparagine and aspartic acid (U.S. Pat. No. 6,960,455). PEP is known to be mostly consumed via the sugar PTS system. Up to 50% of the total PEP is consumed via the glucose PTS system in a minimal medium containing glucose as a carbon source (Microb. Cell Fact. (2005) 4:14). Therefore, if using a sugar non-PTS system instead of sugar PTS system, intracellular PEP pool can be increased, and the increased PEP can be used for biosynthesis of fermentation products, thereby improving productivity and yield.

In sucrose utilization, the Scr-non PTS system, which requires no PEP consumption upon sucrose uptake, is also more preferred than Scr-PTS system. Practically, Ajinomoto Co. has introduced methods of making threonine, isoleucine and tryptophan using E. coli transformed with EC3132-derived cscBKA (U.S. Pat. No. 6,960,455). DuPont has also produced tyrosine using E. coli K12 transformed with E. coli ATCC13281-derived cscBKAR and sucrose (Appl. Microbiol. Biotechol. (2007) 74:1031-1040).

Meanwhile, mannokinase (Mak) has a kinase activity that converts hexose, including mannose and fructose, to 6-phospho-ester by ATP consumption. In particular, a gene (mak or yajF) encoding the wild-type Mak (Mak-o) of enteric bacteria is known as a cryptic gene, and its activity is greatly increased by sequence mutation in the promoter-35 region of mak (Mak+) (Kornberg H L, J. Mol. Microbiol. Biotechnol. (2001) 3:355-359; Miller B G & Raines R T, Biochemistry (2005) 44:10776-10783). Mak is also able to phosphorylate other substrates such as glucose, sorbose, and glucosamine, in addition to mannose and fructose. However, there have been no reports that Mak affects sucrose metabolism.

BRIEF SUMMARY OF THE INVENTION

To develop microorganisms capable of utilizing sucrose with high efficiency, the present inventors had investigated genes expected to be involved in sucrose metabolism, and they found that mannokinase plays an important role in sucrose metabolism, that is, even though E. coli having inactivated mannokinase is introduced with the intact csc regulon, its sucrose utilization rate is reduced in comparison to the wild type E. coli, thereby completing the present invention.

An object of the present invention is to provide a microorganism belonging to the genus Escherichia having improved L-amino acid productivity, which utilizes sucrose as a main carbon source. More particularly, an object of the present invention is to provide a microorganism belonging to the genus Escherichia that has the improved L-amino acid productivity and sucrose-assimilating ability, which is prepared by imparting the activities of sucrose permease, sucrose hydrolase and sucrose transcriptional regulator to a sucrose non-assimilative microorganism and enhancing mannokinase activity.

Another object of the present invention is to provide a method for producing an L-amino acid using the microorganism belonging to the genus Escherichia.

When the microorganism belonging to the genus Escherichia that has the improved L-amino acid productivity and sucrose-assimilating ability according to the present invention is used for the production of L-amino acids, sucrose can be used as a main carbon source instead of starch sugar usually used in industrial fermentation, thereby coping with the rapid rise in global prices of grain as well as producing L-amino acids with high yield.

BRIEF DESCRIPTION OF THE DRAWINGS/FIGURES

Figure 2:
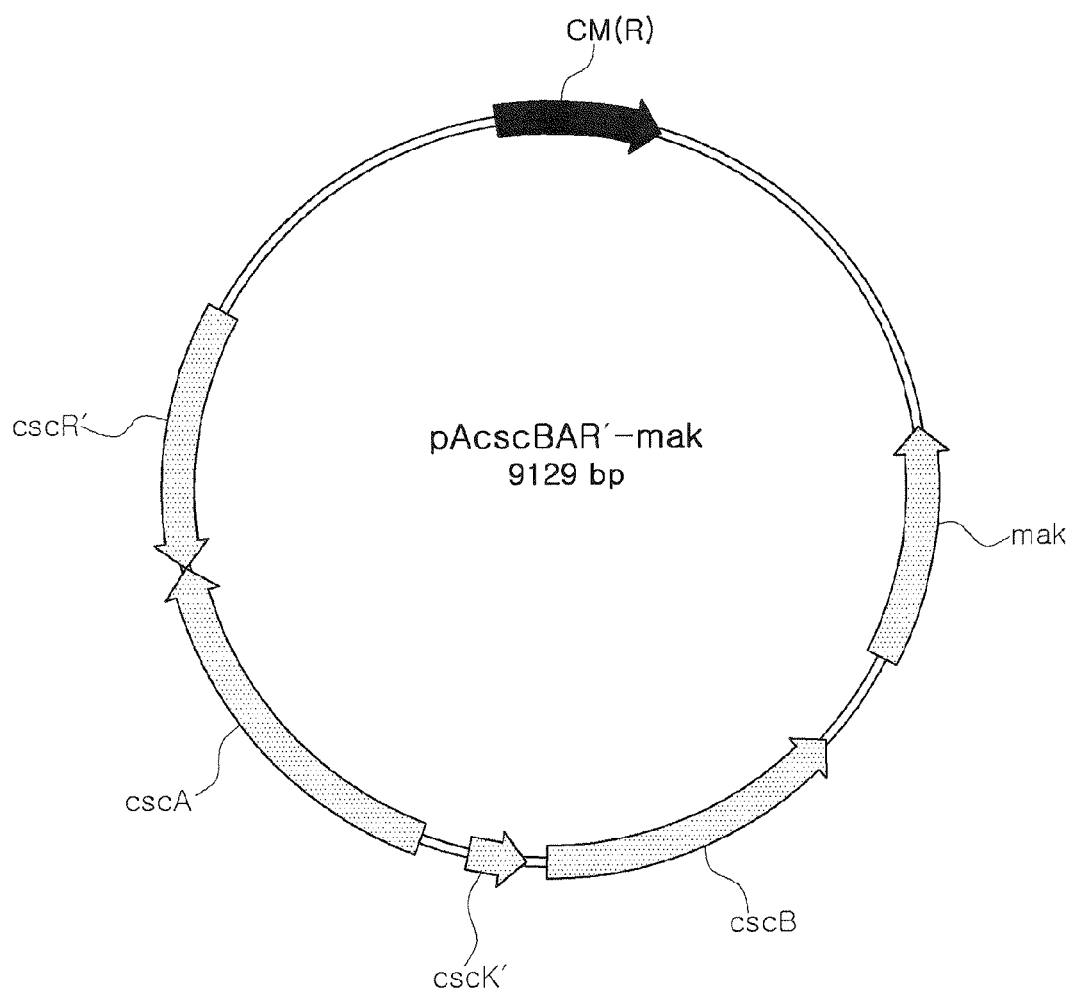

FIG. 1 is a schematic diagram showing the scr regulon, in which p represents promoters, Ko1 and Yo2o3 represent operators, and t represents terminators; and FIG. 2 shows the construction of recombinant plasmid pAcscBAR'-mak containing cscBAR'-mak.

DETAILED DESCRIPTION OF THE INVENTION

In an aspect, to achieve the above objects, the present invention relates to a microorganism belonging to the genus Escherichia that has improved L-amino acid productivity and sucrose-assimilating ability, which is prepared by imparting the activities of sucrose permease (cscB), sucrose hydrolase (cscA) and sucrose transcriptional regulator (cscR) to a sucrose non-assimilative microorganism and enhancing mannokinase activity.

In the present invention, sucrose permease is a peptide having an activity of importing extracellular sucrose, sucrose hydrolase has an activity of hydrolyzing sucrose to glucose and fructose, and sucrose transcriptional regulator has an activity of regulating transcription of genes that encode sucrose permease and sucrose hydrolase. The activities of sucrose permease, sucrose hydrolase and sucrose transcriptional regulator are present in microorganisms having sucrose-assimilating ability, but not present in microorganisms belonging to the genus Escherichia, in particular, industrial strains such as E. coli K12 strain, B strain and C strain.

The methods of imparting the activities of sucrose permease, sucrose hydrolase and sucrose transcriptional regulator to the sucrose non-assimilative Escherichia may be performed by a variety of methods well known in the art. Preferably, the method is to introduce the genes encoding sucrose permease, sucrose hydrolase and sucrose transcriptional regulator into a vector, and to transform the sucrose non-assimilative Escherichia having L-amino acid productivity with the recombinant vector. The gene encoding sucrose permease, the gene encoding sucrose hydrolase, and the gene encoding sucrose transcriptional regulator may be derived from a microorganism having a sucrose-assimilating ability, preferably the genus Escherichia having a sucrose-assimilating ability, and more preferably E. coli having a sucrose-assimilating ability. Examples of E. coli having a sucrose-assimilating ability include E. coli ATCC9637 (Alterthum F & Ingram L O, Appl. Environ. Microbiol. (1989) 55:1943-1948) or the like. The gene (cscB) encoding sucrose permease, the gene (cscA) encoding sucrose hydrolase, and the gene (cscR) encoding sucrose transcriptional regulator that are obtained from the E. coli ATCC9637 are represented by SEQ ID NOs. 4, 6, and 7, respectively.

In a specific embodiment, the present inventors may introduce a cscBAR gene encoding sucrose permease, sucrose hydrolase and sucrose transcriptional regulator, which includes the cscB, cscA, and cscR genes of SEQ ID NOs. 4, 6 and 7 derived from the csc regulon, into a vector, and then transform the sucrose non-assimilative Escherichia having L-amino acid productivity with the recombinant vector.

In the present invention, mannokinase refers to a peptide having an activity of converting hexose such as mannose to 6-phospho-ester using ATP. The present invention is characterized in that the sucrose non-assimilative Escherichia has enhanced (or increased) mannokinase activity in comparison to the intrinsic activity of mannokinase. The "intrinsic activity" means an activity of the sucrose non-assimilative Escherichia, which is not modified by any genetic manipulation or alteration. In addition, the "enhanced" or "increased" means an improvement in the intrinsic activity of the sucrose non-assimilative Escherichia.

The method of enhancing (or increasing) the mannokinase activity of the present invention may be performed by a variety of methods well known in the art. Examples of the method include, but are not limited to, a method of increasing the copy number of base sequence encoding mannokinase by additionally inserting a polynucleotide containing a base sequence encoding mannokinase into a chromosome, or introducing the polynucleotide into a vector system, a method of replacement with a strong promoter, a method of introducing mutations in the promoter, and a method of gene mutation. In a specific embodiment, to enhance the mannokinase activity of the microorganism belonging to the genus Escherichia that has amino acid productivity, the mannokinase-encoding gene is introduced into a vector to transform the microorganism belonging to the genus Escherichia, thereby increasing the copy number of the gene.

The mannokinase-encoding gene is any gene that has a base sequence being operable in the sucrose non-assimilative Escherichia, and preferably a mak gene encoding the wild-type Mak of enteric bacteria (Mak-o). In a specific embodiment, a polynucleotide having a base sequence of SEQ ID NO. 15 (GenBank accession number AC000091) derived from E. coli was preferably used. Meanwhile, it will be apparent to those skilled in the art that the mannokinase-encoding gene can be modified to some degree as long as it retains its activity. It will be readily understood by those skilled in the art that the base sequence retaining 70% or more homology by the artificial modification is equivalent to that derived from the base sequence of the present invention, as long as it retains the activity desired in the present invention.

In the present invention, to additionally improve the L-amino acid productivity and sucrose-assimilating ability, a method of increasing the copy number of the gene that encodes a peptide having activities of mannokinase, sucrose permease, sucrose hydrolase and sucrose transcriptional regulator, a method of improving a promoter, random mutagenesis, or site-directed mutagenesis may be used. In the specific embodiment of the present invention, random mutagenesis was induced in the gene cluster containing the base sequences encoding mannokinase, sucrose permease, sucrose hydrolase and sucrose transcriptional regulator by hydroxylamine treatment (Sikorski R S & Boeke J D, Methods *Enzymol.* (1991) 194:302-318).

Therefore, in one preferred embodiment, the present invention relates to a microorganism belonging to the genus *Escherichia* having improved L-amino acid productivity and sucrose-assimilating ability, in which the mutation in its base sequence or amino acid sequence is induced by the above mutagenesis. Preferably, the mutant is a mutant having one or more mutations in the base sequences of mannokinase, sucrose permease, sucrose hydrolase and sucrose transcriptional regulator. More preferably, the mutant is a mutant having one or more mutations in the amino acid sequences of mannokinase, sucrose permease, sucrose hydrolase and sucrose transcriptional regulator. Most preferably, the mutant is a mutant having substitution of histidine with tyrosine at position 130 of the amino acid sequence of sucrose transcriptional regulator. Preferably, the mutant has a mutated sucrose transcriptional regulator, encoded by the base sequence represented by SEQ ID NO. 17.

A microorganism belonging to the genus *Escherichia* that has improved L-amino acid productivity and sucrose-assimilating ability according to the present invention may be provided by introducing the mutant into the vector, and transforming the sucrose non-assimilative *Escherichia* having L-amino acid productivity with the recombinant vector. In a specific embodiment, the present inventors used a pAcscBAR'-mak plasmid containing a base sequence represented by SEQ ID NO. 18 to transform the sucrose non-assimilative *Escherichia* into a microorganism belonging to the genus *Escherichia* that has improved L-amino acid productivity and sucrose-assimilating ability.

As used herein, the term "vector" is a nucleic acid compound used for the preparation of the microorganism belonging to the genus *Escherichia* according to the present invention, prepared by introducing the genes encoding sucrose permease, sucrose hydrolase, sucrose transcriptional regulator and mannokinase into a host cell, sucrose non-assimilative *Escherichia*, and the vector includes typical essential expression factors for the expression of desired protein. Specifically, the vector includes expression regulatory elements such as a promoter, an operator, an initiation codon, a termination codon, and a polyadenylation signal, which can be modified in various forms. In addition, the vector may include an enhancer sequence or secretory sequence. Examples of the commonly used vectors may include natural or recombinant plasmids, cosmids, viruses, and bacteriophages. For example, the phage vector or cosmid vector may include pWE15, M13, λEMBL3, λEMBL4, λFIXII, λDASHII, λZAPII, λgt10, λgt11, Charon4A, and Charon21A, and the plasmid vector include pBR, pUC, pBluescriptII, pGEM, pTZ, pCL and pET-type plasmids. The vectors to be used are not particularly limited, and any known expression vectors may be used.

pACYC177, pACYC184, pCL, pECCG117, pUC19, pBR322 and pMW118 vectors are preferred.

As used herein, the term "transformation" means a method in which a gene is introduced into a host cell to be expressed in the host cell. The transformed genes, if they are in the state of being expressed in the host cell, comprise any of the genes inserted in the chromosome of the host cell or positioned in other parts of the chromosome. In addition, the gene comprises DNA and RNA as a polynucleotide capable of encoding a polypeptide. As long as the gene can be introduced in the host cell and expressed therein, the gene is introduced in any type. For example, the gene can be introduced into the host cell in the type of expression cassette which is polynucleotide expressome comprising by itself whole elements for expressing the gene. The expression cassette comprises a promoter which is operably connected to the gene, transcription termination signal, ribosome binding site and translation termination signal. The expression cassette can be in the type of the expression vector capable of self cloning. The gene also can be introduced into the host cell by itself or in the type of polynucleotide expressome to be operably connected to the sequence necessary for expression in the host cell.

The microorganism of the present invention refers to a microorganism having both improved L-amino acid productivity and sucrose-assimilating ability, which is prepared by imparting the activities of sucrose permease, sucrose hydrolase and sucrose transcriptional regulator to a sucrose non-assimilative microorganism having L-amino acid productivity, and enhancing the mannokinase activity. Therefore, the microorganism of the present invention comprises any prokaryotic or eukaryotic microorganism possessing the above properties, and examples thereof include the microorganism strains belonging to the genus *Escherichia, Erwinia, Serratia, Providencia, Corynebacterium*, and *Brevibacterium*. The microorganism of the present invention is preferably a microorganism belonging to the genus *Escherichia*, and more preferably *E. coli*.

In the present invention, "L-amino acid" is L-threonine, O-succinyl-homoserine, O-acetyl-homoserine, L-methionine, L-lysine, L-homoserine, L-isoleucine, L-valine, L-tryptophan or the like. Preferably, the L-amino acid is L-threonine, O-succinyl-homoserine, O-acetyl-homoserine, and L-tryptophan.

In one specific embodiment, the present inventors transformed the *E. coli* ABA5G strain having L-threonine productivity using a vector having a base sequence of SEQ ID NO. 18, which contains the cscBAR'-mak gene cluster of *E. coli* having L-threonine productivity. The prepared strain was designated as *E. coli* CA03-0308, and deposited in the international depository authority, Korean Culture Center of Microorganisms, which is the Subsidiary Culture Collection of the Korean Federation of Culture Collections, (located at 361-221, Hongje-1-dong, Seodaemon-gu, Seoul, Korea) on Dec. 23, 2008, and assigned accession number KCCM-10978P.

In another aspect, the present invention relates to a method for producing amino acids by culturing the microorganism belonging to the genus *Escherichia* that has the improved L-amino acid productivity and sucrose-assimilating ability in a medium containing sucrose as a main carbon source.

Specifically, the present invention relates to a method for producing L-amino acids using the microorganism belonging to the genus *Escherichia* in a medium containing sucrose as a carbon source, comprising the steps of inoculating and culturing the microorganism having sucrose-assimilating ability and L-amino acid productivity in a culture medium that totally or partially contains sucrose as a carbon source; and separating L-amino acids from the culture medium.

The culturing procedures of the present invention may be conducted in suitable media and under culture conditions known in the art. According to strains used, the culturing procedures can be readily adjusted by those skilled in the art. Examples of the culturing procedures include batch type, continuous type and fed-batch type manners, but are not limited thereto. The media used in the culture method should preferably meet the requirements of a specific strain.

The medium used in the present invention contains sucrose as a main carbon source. The sucrose used as a main carbon source may be supplied in the form of molasses containing a high concentration of sucrose, and the medium may contain a proper amount of various carbon sources without limitation, in addition to sucrose or molasses. The nitrogen source may be used either singly or in combinations. To the medium, phosphorus sources such as potassium dihydrogen phosphate, dipotassium hydrogen phosphate or corresponding sodium-containing salts may be added. In addition, the medium may contain metal salts such as magnesium sulfate and ferrous sulfate. Further, the medium may be supplemented with amino acids, vitamins, and appropriate precursors. These media or precursors may be added to cultures by a batch type or continuous type method.

During cultivation, ammonium hydroxide, potassium hydroxide, ammonia, phosphoric acid, and sulfuric acid may be properly added so as to adjust the pH of the cultures. Defoaming agents such as fatty acid polyglycol ester may be properly added so as to reduce the formation of foams in cultures. To maintain the cultures in aerobic states, oxygen or oxygen-containing gas may be injected into the cultures. To maintain the cultures in anaerobic and microaerobic states, no gas may be injected or nitrogen, hydrogen, or carbon dioxide gas may be injected into the cultures. The cultures are maintained at 27 to 37° C., and preferably at 30 to 35° C. The cultivation may be continued until a desired amount of the desired material is obtained, and preferably for 10 to 100 hrs.

The method of collecting and recovering the amino acids produced in the cultivation step of the present invention may be performed by a proper method known in the art, depending on the culturing procedures, for example, batch type, continuous type or fed-batch type, so as to collect the desired amino acid from the culture medium.

Hereinafter, the present invention will be described in more detail with reference to Examples. However, these Examples are for illustrative purposes only, and the invention is not intended to be limited by these Examples.

Example 1

Establishment and Cloning of Sucrose-Assimilative Gene, csc Regulon

A regulon containing the cscBKAR gene (GenBank accession number X81461) encoding the Scr-non PTS system which requires no PEP (phosphoenolpyruvate) consumption upon sucrose uptake was amplified by PCR using a genomic DNA of *E. coli* W strain (ATCC9637, USA) as a template. A primer of SEQ ID NO. 1, having the EagI restriction site and a primer of SEQ ID NO. 2 having the XbaI restriction site were used to amplify four types of genes, which are consecutively present on the genome, as a single polynucleotide.

SEQ ID NO. 1:
5'-CTTACGGCCGGAGTACATTTGAGCGACTGT-3'

SEQ ID NO. 2:
5'-CGACTCTAGACTCGTTGGCGAGAACAGAGG-3'

PCR was performed under the conditions including denaturation at 94° C. for 3 min, 25 cycles of denaturation at 94° C. for 30 sec, annealing at 56° C. for 30 sec, and polymerization of at 72° C. for 5 min, and then polymerization for at 72° C. for 7 min. As a result, a polynucleotide of 5199 bp was obtained. The obtained polynucleotide was treated with EagI and XbaI restriction enzymes, and then cloned into a pACYC184 vector. Thereafter, *E. coli* DH5α was transformed with the vector, and spread on a MacConkey agar plate containing 1% sucrose. Of colonies, deep purple colonies were selected, and then a plasmid was obtained from the colonies.

Example 2

Determination of Base Sequence of Obtained cscBKAR Gene

The obtained plasmid was designated as pAcscBKAR, and the DNA base sequence (SEQ ID NO. 3) of cscBKAR cloned into the EagI and XbaI sites were analyzed. It was determined that the positions 141 to 1388 of the base sequence were cscB (SEQ ID NO. 4), the positions 1460 to 2374 cscK (SEQ ID NO. 5), the positions 2590 to 4023 cscA (SEQ ID NO. 6), and the positions 4031 to 5026 cscR(SEQ ID NO. 7).

Example 3

Construction of MG1655 mak Gene-Deleted Strain

To investigate crucial genes involved in sucrose metabolism, candidate genes expected to be involved in sucrose metabolism were selected, and mutant *E. coli* K12 having each deleted gene was constructed. One-step inactivation (*Proc. Natl. Acad. Sci.* (2000) 97:6640-6645) was performed to delete each gene, thereby constructing the mutant *E. coli* K12, and an antibiotic resistance marker gene was removed. In particular, to construct a mak-deleted strain, PCR was performed using a pair of primers of SEQ ID NOs. 8 and 9 and a pKDA4 plasmid (GenBank No. AY048743). The obtained DNA fragment was electroporated into a competent cell, the wild-type *E. coli* K12 containing pKD46 (GenBank No. AY048746). Then, the strains showing a resistance to kanamycin were subjected to PCR, and the deletion of mak gene was examined. A pCP20 plasmid was introduced to remove an antibiotic resistance marker gene.

Examples

SEQ ID NO. 8:
5'-GTGCGTATAGGTATCGATTTAGGCGGCACCAAAACTGAAGTGATT

GCACTGTTGCAGCATTACACGTCTTG-3'

SEQ ID NO. 9:
5'-TTACTCTTGTGGCCATAACCACGCAGCGCCGCGTACGCCGCTGGA

ATCACCACTTAACGGCTGACATGGGA-3'

Example 4

Introduction of pAcscBKAR into MG1655 mak Gene-Deleted Strain and Analysis of Sucrose Assimilation

*E. coli* K12 with a deletion of mak gene that was expected to affect sucrose metabolism was constructed according to Example 3, and then transformed with pAcscBKAR plasmid. The pAcscBKAR plasmid-introduced transformant was cultured on a LB solid media in a 33° C. incubator overnight. One loop of the strain was inoculated in 25 mL of a titration medium containing sucrose of Table 1, and then cultured in a 33° C. incubator at 200 rpm for 36 hrs. OD value and sugar consumption of the culture medium was measured, and the results are shown in Table 2.

TABLE 1

| Composition | Concentration (per liter) |
| --- | --- |
| Sucrose | 70 g |
| $KH_2PO_4$ | 2 g |
| $(NH_4)_2SO_4$ | 25 g |
| $MgSO_4 \cdot 7H_2O$ | 1 g |
| $FeSO_4 \cdot 7H_2O$ | 5 mg |
| $MnSO_4 \cdot 4H_2O$ | 5 mg |
| Yeast Extract | 2 g |
| Calcium carbonate | 30 g |
| pH | 6.8 |

TABLE 2

| Strain | OD | Sugar consumption (g/L) |
| --- | --- | --- |
| MG1655/pAcscBKAR | 26.0 | 33.1 |
| MG1655Δmak/pAcscBKAR | 24.2 | 24.9 |

As shown in Table 2, it was found that the mak-deleted, csc regulon-introduced strain utilized 24.9 g/L of sucrose for 36 hrs, and non-mak-deleted, csc regulon-introduced wild-type strain utilized 33.1 g/L of sucrose, indicating that the sucrose consumption rate of the mak-deleted strain is approximately 1.3 times less than that of non-mak-deleted strain. Therefore, it was suggested that mak is a crucial gene in sucrose metabolism.

Example 5 pAcscBAR-mak Construction

To develop efficient sucrose-assimilative strains, a vector overexpressing both mak and csc regulon was constructed. At this time, cscK was excluded from the csc regulon. First, pAcscBAR was constructed, and the mak gene was cloned into pAcscBAR.

Specifically, a pair of primers of SEQ ID NOs. 10 and 11 was used to perform PCR under the conditions of Example 1 to amplify a polynucleotide of cscB region, where cscK was removed. As a result, a polynucleotide of 1521 bp was obtained.

SEQ ID NO. 10:
5'-CGCGATATCTAGCATATGCCGGGTACCGCACTAGTTGAGAGTAA ACGGCGAAGT-3'

SEQ ID NO. 11:
5'-ATTCGGCCGGAGCCCTGCAGGTGCACGAGTACATTTGAGCGAC TGT-3'

The obtained polynucleotide and pAcscBKAR were treated with the restriction enzymes EcoRV and EagI, respectively and connected to each other to construct a pAcscBAR plasmid. *E. coli* DH5α was transformed with the vector, and colonies containing pAcscBAR were screened from the colonies on LB medium by PCR, so as to obtain a pAcscBAR plasmid. The base sequence (SEQ ID NO. 12) of cscBAR linked at the XbaI and EagI restriction sites of the obtained pAcscBAR plasmid was analyzed, and no mutation was found.

Subsequently, PCR was performed using the genomic DNA of *E. coli* W3110 as a template and a pair of primers of SEQ ID NOs. 13 and 14 in the same manners as in Example 1 to amplify the polynucleotide containing mak. A polynucleotide of 1388 bp was obtained, and the PCR product was cloned at the PstI and EagI restriction sites of pAcscBAR to construct pAcscBAR-mak.

SEQ ID NO. 13:    5'-CACTGCAGTGGGGTAAATGCCATCG-3'

SEQ ID NO. 14:    5'-AACGGCCGTCTCGGTGCTCATTACT-3'

*E. coli* DH5α was transformed with pAcscBAR, and colonies containing pAcscBAR-mak were screened from the colonies on LB medium by PCR, so as to obtain a pAcscBAR-mak plasmid. The base sequence (SEQ ID NO. 16) of cscBAR-mak linked at the XbaI and EagI restriction sites of the obtained pAcscBAR-mak plasmid was analyzed, and no mutation was found.

Example 6

Introduction of pAcscBAR-mak into Threonine-Producing Strain

In order to confirm whether threonine-producing *E. coli* grows on sucrose and efficiently produces threonine by transformation of pAcscBAR-mak, a threonine-producing strain, ABA5G (KFCC 10718) was transformed with the plasmid. Colonies having the plasmid containing the sucrose assimilation-related gene were screened from the obtained colonies by PCR. The screened colonies were incubated on LB solid medium in a 33° C. incubator overnight. One loop of the strain was inoculated in 25 mL of a titration medium of Table 1, and then cultured in a 33° C. incubator at 200 rpm for 30 hrs. Subsequently, OD value and sugar consumption of the culture medium was measured, and the results are shown in Table 3.

TABLE 3

| Parental strain | OD | Sugar consumption (g/L) | L-threonine (g/L) |
| --- | --- | --- | --- |
| pAcscBKAR | 9.2 | 18.7 | 6.0 |
| pAcscBAR-mak | 10.8 | 27.7 | 9.7 |

As shown in Table 3, when the ABA5G strain containing pAcscBKAR was cultured for 30 hrs, it utilized 18.7 g/L of sucrose, and produced 6.0 g/L of L-threonine, but the ABA5G strain containing pAcscBAR-mak utilized 27.7 g/L of sucrose, and produced 9.7 g/L of L-threonine. That is, the sucrose consumption rate of the ABA5G containing pAcscBAR-mak was approximately 1.5 times more than that of the ABA5G containing pAcscBKAR, and the threonine productivity of the ABA5G containing pAcscBAR-mak increased to 3.7 g/L more than that of the ABA5G containing pAcscBKAR.

Example 7

Enhancement of Mak Activity by Introduction of cscBAR-Mak

To confirm an increase or enhancement in the mannokinase activity of the ABA5G strain containing pAcscBAR-mak as compared to the parental strain ABA5G, the fructokinase activity was measured (Copeland L et al., *Plant Physiol.* (1978) 62:291-294). This measurement of fructokinase activity is a method of measuring the fructokinase activity of mannokinase through coupling reaction using mannokinase, phosphoglucose isomerase and glucose-6-phosphate dehydrogenase and using a fructose as an initial substrate. The supernatant was obtained by sonication and centrifugation of the ABA5G strains containing each of pAcscBAR and pAcscBAR-mak cultured in LB for 24 hrs, and used as an enzyme liquid. Protein concentration was determined by the Bradford assay. Enzyme reaction was maintained for 30 min, and the change in absorbance was measured at OD 340 nm to measure NADPH produced by the coupling reaction. The activity was calculated using NADPH absorption coefficient of 6.22 $cm^{-1}$ $mM^{-1}$. 1 unit of mannokinase is defined as an amount of enzyme that catalyzes 1 mg of total protein per 1 min to produce 1 nM NADPH by the above enzyme activity measurement. The result is shown in Table 4.

TABLE 4

| Parental strain ABA5G | Units (nM/mg/Min) |
|---|---|
| pAcscBAR | 0.3 |
| pAcscBAR-mak | 3.7 |

As shown in Table 4, the mannokinase activity of ABA5G containing pAcscBAR-mak was increased or enhanced approximately 12 times more than that of ABA5G containing pAcscBAR only.

Example 8

Introduction of cscBAR-mak Mutation

To improve sucrose assimilation and threonine productivity, chemical random mutagenesis was performed to obtain a mutated sucrose-assimilating gene by treatment of hydroxylamine (Sikorski R S & Boeke J D, *Methods Enzymol.* (1991) 194:302-318). First, 1 M hydroxylamine, 2 mM EDTA, 100 mM sodium chloride, and 50 mM sodium pyrophosphate were added to prepare a mutagenesis solution, and then 25 µl of target DNA (0.2 mg/ml) was added to 1 ml of mutagenesis solution. The DNA fragment containing 5887 bp of cscBAR-mak, which was obtained from the pAcscBAR-mak plasmid using restriction enzymes EagI and XbaI, was used as the target DNA. 500 µl of the DNA fragment in the mutagenesis solution was purified at 75° C. at 30 min, 1 hr, 2 hr, and 4 hr using a purification column. DNA treated with hydroxylamine and the pACYC 184 vector treated with restriction enzymes EagI and XbaI were linked to each other using a T4 DNA ligase, and transformed into the threonine-producing strain ABASG. The transformed strain was spread on a MacConkey agar plate containing 0.1% low concentration of sucrose, and cultured at 37° C. for a day. Of colonies, deep purple colonies were selected.

The selected colonies were cultured in the titration medium of Table 1, and threonine productivity and sucrose utilization rate were evaluated. Finally, the strain showing excellent threonine productivity and sucrose utilization was selected. A plasmid was obtained from the selected strain, and base sequence analysis was performed. As a result, substitution of C to T at position 388 in cscR of the strain was observed, and therefore a mutation from histidine to tyrosine occurred at position 130 of the amino acid sequence. The sucrose transcriptional regulator cscR having the mutation was encoded by the base sequence of SEQ ID NO. 17.

Example 9

Improvement of L-Threonine Productivity by Introduction of pAcscBAR'-mak

The pAcscBAR'-mak (SEQ ID NO. 18) plasmid containing cscR mutation (SEQ ID NO. 17) was transformed into ABA5G to perform a flask titration test. The strain was cultured on LB solid medium and in a 33° C. incubator overnight. One loop of the strain was inoculated in 25 mL of a titration medium of Table 1, and then cultured in a 33° C. incubator at 200 rpm for 30 hrs. The results are shown in Table 5.

TABLE 5

| Parental strain ABA5G | OD | Sugar consumption (g/L) | L-threonine (g/L) |
|---|---|---|---|
| pAcscBKAR | 9.2 | 18.7 | 6.0 |
| pAcscBAR-mak | 10.8 | 27.7 | 9.7 |
| pAcscBAR'-mak | 10.3 | 33.4 | 12.4 |

As shown in Table 5, when the strains were cultured for 30 hrs, the ABA5G strain containing pAcscBKAR utilized 18.7 g/L of sucrose and produced 6.0 g/L of L-threonine, but the ABA5G strain containing pAcscBAR'-mak was utilized 33.4 g/L of sucrose and produced 12.4 g/L of L-threonine. That is, the sucrose utilization rate and threonine productivity of the ABA5G strain containing pAcscBAR'-mak increased approximately 1.8 times and 6.4 g/L more than those of the ABA5G strain containing pAcscBKAR, respectively. In addition, the sucrose utilization rate and threonine productivity of the ABA5G strain containing pAcscBAR'-mak increased approximately 1.2 times and 2.7 g/L more than those of the ABA5G strain containing pAcscBAR-mak, respectively. Therefore, the recombinant strain containing cscBAR'-mak was found to show the improved sucrose utilization and L-threonine productivity. The transformed microorganism was designated as CA03-0308, and deposited in the international depository authority, Korean Culture Center of Microorganisms, which is the Subsidiary Culture Collection of the Korean Federation of Culture Collections, (located at 361-221, Hongje-1-dong, Seodaemon-gu, Seoul, Korea) on Dec. 23, 2008, and assigned accession number KCCM-10978P.

Example 10

Improvement of O-Succinyl-Homoserine Productivity by Introduction of pAcscBAR'-mak The O-succinyl-homoserine-producing strain, CJM-11A (KCCM-10922P) disclosed in US patent application publication No. 2009/0253187 was transformed with the pAcscBAR'-mak constructed in Example 8, and spread on a MacConkey agar plate containing 0.1% low concentration of sucrose, followed by cultivation at 37° C. for one day. Of the colonies, the deep purple colonies were selected.

The selected transformant was cultured on LB solid medium and in a 33° C. incubator overnight. One loop of the strain was inoculated in 25 mL of a titration medium containing sucrose of Table 1, and then cultured in a 33° C. incubator at 200 rpm. The results are shown in Table 6.

TABLE 6

| Parental strain CJM-11A | OD | Sugar consumption (g/L) | O-Succinyl-homoserine (g/L) |
|---|---|---|---|
| pAcscBKAR | 6.8 | 30.2 | 12.3 |
| pAcscBAR-mak | 6.8 | 44.8 | 18.2 |
| pAcscBAR'-mak | 7.5 | 50.4 | 20.5 |

As shown in Table 6, when the strains were cultured for 48 hrs, the parental strain, CJM-11A containing pAcscBKAR utilized 30.2 g/L of sucrose and produced 12.3 g/L of O-succinyl-homoserine, but the CJM-11A strain containing pAcscBAR'-mak utilized 50.4 g/L of sucrose and produced 20.5 g/L of O-succinyl-homoserine, indicating that the sucrose utilization rate and O-succinyl-homoserine productivity increased approximately 1.7 times and 8.2 g/L more than those of the CJM-11A strain containing pAcscBKAR, respectively. That is, the recombinant strain containing cscBAR'-mak was found to show improved sucrose utilization and O-succinyl-homoserine productivity.

Example 11

Improvement of O-Acetyl-Homoserine Productivity by Introduction of pAcscBAR'-mak The O-acetyl-homoserine-producing strain, CJM-X (KCCM-10921P) disclosed in US patent application publication No. 2009/0253186 was transformed with the pAcscBAR'-mak constructed in Example 8, and spread on a MacConkey agar plate containing 0.1% low concentration of sucrose, followed by cultivation at 37° C. for one day. Of the colonies, the deep purple colonies were selected.

The selected transformant was cultured on LB solid medium and in a 33° C. incubator overnight. One loop of the strain was inoculated in 25 mL of a titration medium containing sucrose of Table 1, and then cultured in a 33° C. incubator at 200 rpm. The results are shown in Table 7.

TABLE 7

| Parental strain CJM-x | OD | Sugar consumption (g/L) | O-acetyl-homoserine (g/L) |
|---|---|---|---|
| pAcscBKAR | 13.5 | 29.9 | 10.7 |
| pAcscBAR-mak | 12.3 | 42.9 | 15.4 |
| pAcscBAR'-mak | 13.6 | 53.5 | 19.5 |

As shown in Table 7, when the strains were cultured for 48 hrs, the parental strain, CJM-X containing pAcscBKAR utilized 29.9 g/L of sucrose and produced 10.7 g/L of O-acetyl-homoserine (hereinbelow, referred to as OAH), but the CJM-X strain containing pAcscBAR'-mak utilized 53.5 g/L of sucrose and produced 15.4 g/L of OAH, indicating that the sucrose utilization rate and OAH productivity increased approximately 1.8 times and 8.8 g/L more than those of the CJM-X strain containing pAcscBKAR, respectively. That is, the recombinant strain containing cscBAR'-mak was found to show improved sucrose utilization and OAH productivity.

Example 12

Improvement of L-Tryptophan Productivity by Introduction of pAcscBAR'-mak

The L-tryptophan-producing strain, CJ285 (KCCM-10534, deposited in Korean Culture Center of Microorganisms on Nov. 28, 2003) was transformed with the pAcscBAR'-mak constructed in Example 8, and spread on a MacConkey agar plate containing 0.1% low concentration of sucrose, followed by cultivation at 37° C. for one day. Of colonies, deep purple colonies were selected.

The selected transformant was cultured on LB solid medium and in a 37° C. incubator overnight. One loop of the strain was inoculated in 25 mL of a titration medium containing sucrose of Table 8, and then cultured in a 37° C. incubator at 200 rpm. The results are shown in Table 9.

TABLE 8

| Composition | Concentration (per liter) |
|---|---|
| Sucrose | 60 g |
| $KH_2PO_4$ | 2 g |
| $(NH_4)_2SO_4$ | 20 g |
| $MgSO_4 \cdot 7H_2O$ | 1 g |
| $Na_3C_6H_5O_7 \cdot 2H_2O$ | 5 g |
| NaCl | 1 g |
| Yeast Extract | 2.5 g |
| Calcium carbonate | 40 g |

TABLE 9

| Parental strain CJ285 | OD | Sugar consumption (g/L) | L-tryptophan (g/L) |
|---|---|---|---|
| pAcscBKAR | 19.6 | 24.7 | 4.9 |
| pAcscBAR-mak | 22.8 | 33.2 | 6.8 |
| pAcscBAR'-mak | 24.1 | 37.1 | 8.9 |

As shown in Table 9, when the strains were cultured for 60 hrs, the parental strain, CJ285 containing pAcscBKAR utilized 24.7 g/L of sucrose and produced 4.9 g/L of L-tryptophan, but the CJ285 strain containing pAcscBAR'-mak utilized 37.1 g/L of sucrose and produced 8.9 g/L of L-tryptophan, indicating that the sucrose utilization rate and L-tryptophan productivity increased approximately 1.5 times and 4.0 g/L more than those of the CJ285 strain containing pAcscBKAR, respectively. That is, the recombinant strain containing cscBAR'-mak was found to show improved sucrose utilization and L-tryptophan productivity.

It will be apparent to those skilled in the art that various modifications and changes may be made without departing from the scope and spirit of the invention. Therefore, it should be understood that the above embodiment is not limitative, but illustrative in all aspects. The scope of the invention is defined by the appended claims rather than by the description preceding them, and therefore all changes and modifications that fall within metes and bounds of the claims, or equivalents of such metes and bounds are therefore intended to be embraced by the claims.

When the microorganism belonging to the genus *Escherichia* that has the improved L-amino acid productivity and sucrose-assimilating ability according to the present invention is used for the production of L-amino acids, sucrose can be used as a main carbon source instead of starch sugar usually used in industrial fermentation, thereby coping with the rapid rise in global prices of grain as well as producing L-amino acids with high yield.

What is claimed is:

1. A transformed microorganism belonging to the genus *Escherichia*,
comprising csc genes from *E. coli* encoding sucrose permease, sucrose hydrolase, and sucrose transcriptional regulator,
wherein the transformed microorganism does not contain a functional fructokinase gene,
wherein the transformed microorganism overexpresses a gene encoding mannokinase activity compared to a non-transformed microorganism, and
wherein the transformed microorganism is a sucrose assimilative microorganism.

2. The transformed microorganism according to claim 1, wherein the sucrose permease, sucrose hydrolase, and sucrose transcriptional regulator genes are provided as the cscB, cscA and cscR genes, respectively, of a cscBKAR regulon in which the cscK gene has been removed.

3. The transformed microorganism according to claim 1, wherein the gene encoding the mannokinase comprises the base sequence of SEQ ID NO. 15.

4. The transformed microorganism according to claim 1, wherein the csc genes encoding the sucrose permease, sucrose hydrolase and sucrose transcriptional regulator comprise the base sequences of SEQ ID NOs. 4, 6 and 7, respectively.

5. The transformed microorganism according to claim 1, wherein the sucrose transcriptional regulator is a mutated sucrose transcriptional regulator having a substitution of histidine with tyrosine at position 130 of the amino acid sequence of a wild-type sucrose transcriptional regulator,
wherein the wild-type sucrose transcriptional regulator is encoded by a base sequence of SEQ ID NO. 7.

6. The transformed microorganism according to claim 5, wherein the sucrose transcriptional regulator is encoded by a base sequence of SEQ ID NO. 17.

7. The transformed microorganism according to claim 1, wherein the microorganism is transformed with a vector comprising the base sequence of SEQ ID NO. 16 encoding sucrose permease, sucrose hydrolase, sucrose transcriptional regulator and mannokinase.

8. The transformed microorganism according to claim 1, wherein the microorganism is transformed with a vector comprising the base sequence of SEQ ID NO. 18 encoding sucrose permease, sucrose hydrolase, sucrose transcriptional regulator variant and mannokinase.

9. The transformed microorganism according to claim 1, wherein the microorganism belonging to the genus *Escherichia* is *E. coli*.

10. The transformed microorganism according to claim 9, wherein the microorganism is *E. coli* CA03-0308 deposited under accession number KCCM10978P.

11. The transformed microorganism according to claim 1, wherein the microorganism can synthesize an L-amino acid selected from the group consisting of L-threonine, O-succinyl-homoserine, O-acetyl-homoserine, L-methionine, L-lysine, L-homoserine, L-isoleucine, L-valine and L-tryptophan.

12. The transformed microorganism according to claim 11, wherein the L-amino acid is selected from the group consisting of L-threonine, O-succinyl-homoserine, O-acetyl-homoserine and L-tryptophan.

13. A method for producing an L-amino acid, comprising:
inoculating and culturing the transformed microorganism according to claim 1 in a culture medium that totally or partially contains sucrose as a carbon source; and
separating the L-amino acid from the culture medium.

14. The method according to claim 13, wherein the L-amino acid is selected from the group consisting of L-threonine, O-succinyl-homoserine, O-acetyl-homoserine, L-methionine, L-lysine, L-homoserine, L-isoleucine, L-valine and L-tryptophan.

* * * * *

SEQUENCE LISTING

```
<160> NUMBER OF SEQ ID NOS: 18

<210> SEQ ID NO 1
<211> LENGTH: 30
<212> TYPE: DNA
<213> ORGANISM: Artificial sequence
<220> FEATURE:
<221> NAME/KEY: gene
<222> LOCATION: (1)..(30)
<223> OTHER INFORMATION: primer for amplification of cscBKAR

<400> SEQUENCE: 1
cttacggccg gagtacattt gagcgactgt                                        30

<210> SEQ ID NO 2
<211> LENGTH: 30
<212> TYPE: DNA
<213> ORGANISM: Artificial sequence
<220> FEATURE:
<221> NAME/KEY: gene
<222> LOCATION: (1)..(30)
<223> OTHER INFORMATION: primer for amplification of cscBKAR

<400> SEQUENCE: 2
cgactctaga ctcgttggcg agaacagagg                                        30

<210> SEQ ID NO 3
<211> LENGTH: 5179
<212> TYPE: DNA
<213> ORGANISM: Escherichia coli (ATCC9637)
<220> FEATURE:
<221> NAME/KEY: gene
<222> LOCATION: (1)..(5179)
<223> OTHER INFORMATION: polynucleotide containing cscBKAR regulon

<400> SEQUENCE: 3
gagtacattt gagcgactgt accagaacat gaatgaggcg tttggattag gcgattatta      60
gcagggctaa gcattttact attattattt tccggttgag ggatatagag ctatcgacaa     120
caaccggaaa aagtttacgt ctatattgct gaaggtacag gcgtttccat aactatttgc     180
tcgcgttttt tactcaagaa gaaaatgcca aatagcaaca tcaggcagac aatacccgaa     240
attgcgaaga aaactgtctg gtagcctgcg tggtcaaaga gtatcccagt cggcgttgaa     300
agcagcacaa tcccaagcga actggcaatt tgaaaaccaa tcagaaagat cgtcgacgac     360
aggcgcttat caaagtttgc cacgctgtat ttgaagacgg atatgacaca aagtggaacc     420
tcaatggcat gtaacaactt cactaatgaa ataatccagg ggttaacgaa cagcgcgcag     480
gaaaggatac gcaacgccat aatcacaact ccgataagta atgcattttt tggccctacc     540
cgattcacaa agaaaggaat aatcgccatg cacagcgctt cgagtaccac ctggaatgag     600
ttgagataac catacaggcg cgttcctaca tcgtgtgatt cgaataaacc tgaataaaag     660
acaggaaaaa gttgttgatc aaaaatgtta tagaaagacc acgtccccac aataaatatg     720
acgaaaaccc agaagtttcg atccttgaaa actgcgataa aatcctcttt ttttacccct     780
cccgcatctg ccgctacgca ctggtgatcc ttatctttaa aacgcatgtt gatcatcata     840
aatacagcgc caaatagcga gaccaaccag aagttgatat ggggactgat actaaaaaat     900
```

```
atgccggcaa agaacgcgcc aatagcatag ccaaaagatc cccaggcgcg cgctgttcca    960
tattcgaaat gaaaatttcg cgccattttt tcggtgaagc tatcaagcaa accgcatccc   1020
gccagatacc cccagccaaa aaacagcgcc cccagaatta gacctacaga aaaattgctt   1080
tgcagtaacg gttcataaac gtaaatcata acggtccgg tcaagaccag gatgaaactc    1140
atacaccaga tgagcggttt cttcagaccg agtttatcct gaacgatgcc gtagaacatc   1200
ataaatagaa tgctggtaaa ctggttgacc gaataaagtg tacctaattc cgtccctgtc   1260
aaccctagat gtccttttcag ccaaatagcg tataacgacc accacagcga ccaggaaata  1320
aaaagagaa atgagtaact ggatgcaaaa cgatagtacg catttctgaa tggaatactc    1380
agtgccataa ttacctgcct gtcgttaaaa aattcacgtc ctatttagag ataagagcga   1440
cttcgccgtt tacttctcac tattccagtt cttgtcgaca tggcagcgct gtcattgccc   1500
ctttcgccgt tactgcaagc gctccgcaac gttgagcgag atcgataatt cgtcgcattt   1560
ctctctcatc tgtagataat cccgtagagg acagacctgt gagtaacccg gcaacgaacg   1620
catctcccgc ccccgtgcta tcgacacaat tcacagacat tccagcaaaa tggtgaactt   1680
gtcctcgata acagaccacc accccttctg cacctttagt caccaacagc atggcgatct   1740
catactcttt tgccagggcg catatatcct gatcgttctg tgttttttcca ctgataagtc   1800
gccattcttc ttccgagagc ttgacgacat ccgccagttg tagcgcctgc cgcaaacaca   1860
agcggagcaa atgctcgtct tgccatagat cttcacgaat attaggatcg aagctgacaa   1920
aacctccggc atgccggatc gccgtcatcg cagtaaatgc gctggtacgc gaaggctcgg   1980
cagacaacgc aattgaacag agatgtaacc attcgccatg tcgccagcag ggcaagtctg   2040
tcgtctctaa aaaagatcg gcactggggc ggaccataaa cgtaaatgaa cgttcccctt    2100
gatcgttcag atcgacaagc accgtggatg tccggtgaca ttcatcttgc ttcagatacg   2160
tgatatcgac tccctcagtt agcagcgttc tttgcattaa cgcaccaaaa ggatcatccc   2220
ccacccgacc tataaaccca cttgttccgc ctaatctggc gattcccacc gcaacgttag   2280
ctggcgcgcc gccaggacaa ggcagtaggc gcccgtctga ttctggcaag agatctacga   2340
ccgcatcccc taaaacccat actttggctg acatttttt cccttaaatt catctgagtt    2400
acgcatagtg ataaacctct ttttcgcaaa atcgtcatgg atttactaaa acatgcatat   2460
tcgatcacaa aacgtcatag ttaacgttaa catttgtgat attcatcgca tttatgaaag   2520
taagggactt tattttttata aaagttaacg ttaacaattc accaaatttg cttaaccagg   2580
atgattaaaa tgacgcaatc tcgattgcat gcggcgcaaa acgccctagc aaaacttcat   2640
gagcaccggg gtaacacttt ctatccccat tttcacctcg cgcctcctgc cgggtggatg   2700
aacgatccaa acggcctgat ctggtttaac gatcgttatc acgcgtttta tcaacatcat   2760
ccgatgagcg aacactgggg gccaatgcac tggggacatg ccaccagcga cgatatgatc   2820
cactggcagc atgagcctat tgcgctagcg ccaggagacg ataatgacaa agacgggtgt   2880
ttttcaggta gtgctgtcga tgacaatggt gtcctctcac ttatctacac cggacacgtc   2940
tggctcgatg gtgcaggtaa tgacgatgca attgcgaag tacaatgtct ggctaccagt    3000
cgggatggta ttcatctcga gaaacagggt gtgatcctca ctccaccaga aggaatcatg   3060
cacttccgcg atcctaaagt gtggcgtgaa gccgacacat ggtggatggt agtcggggcg   3120
aaagatccag gcaacacggg gcagatcctg ctttatcgcg gcagttcgtt gcgtgaatgg   3180
accttcgatc gcgtactggc ccacgctgat gcgggtgaaa gctatatgtg ggaatgtccg   3240
gactttttca gccttggcga tcagcattat ctgatgtttt ccccgcaggg aatgaatgcc   3300
```

```
gagggataca gttaccgaaa tcgctttcaa agtggcgtaa tacccggaat gtggtcgcca    3360
ggacgacttt ttgcacaatc cgggcatttt actgaacttg ataacgggca tgacttttat    3420
gcaccacaaa gcttttttagc gaaggatggt cggcgtattg ttatcggctg gatggatatg    3480
tgggaatcgt caatgccctc aaaacgtgaa ggatgggcag gctgcatgac gctggcgcgc    3540
gagctatcag agagcaatgg caaacttcta caacgcccgg tacacgaagc tgagtcgtta    3600
cgccagcagc atcaatctgt ctctccccgc acaatcagca ataaatatgt tttgcaggaa    3660
aacgcgcaag cagttgagat tcagttgcag tgggcgctga agaacagtga tgccgaacat    3720
tacggattac agctcggcac tggaatgcgg ctgtatattg ataaccaatc tgagcgactt    3780
gttttgtggc ggtattaccc acacgagaat ttagacggct accgtagtat tcccctcccg    3840
cagcgtgaca cgctcgccct aaggatattt atcgatacat catccgtgga agtatttatt    3900
aacgacgggg aagcggtgat gagtagtcga atctatccgc agccagaaga acggaactg    3960 tcgctttatg cctcccacgg agtggctgtg ctgcaacatg gagcactctg gctactgggt    4020
taacataata tcaggtggaa caacggatca acagcgggca agggatccgc gtcactcttc    4080 cccttcacg accttcaata atatgcaatg cagcttcccg cccgataatg tcatgtggaa    4140
gctgaattgt ggtcagcggc ggtaaaaaca gatgcccgac gccaaccaga ttatcaaagc    4200
ccattacggc gacatcctgc gggattcgta ccccttcgc cagaagaacc tgataagcca    4260 caaggctgc gcgatcgtta ccacatatca gaacatcaaa atctggtttg cccggtttga    4320
agtgggcatt gagtaaactt gcgagatcgg tgtagtgatc atcacctgtt gccatgtgaa    4380
attgtttcac ctcagccaga tctcgttcag catcacgcca ggcctgctca aatccctgcc    4440
gacgataccc tgttgccaac gcactttccg gtagccagaa gcataacggt tgacgatagc    4500
ccgccgcgag caaatgctgt gttgattcat attgtgcagt gtaatcatca gggatataac    4560
tgggtaacgc tgggtcatcc gccacacagt tcgccaatac aatattttca ccatacagag    4620
actcaggcag cgtgatatgt cgcagccca ttgtagtata gataatgcca tccggacggt    4680
gggcaagcag ctgacgtgcc gcgcgggcag cgtcatcttc agaaaaaata ttgattaaaa    4740
aactattcca gccgaactcg ctggcggttt gctcaatggc aagcagaata tcaacagaga    4800
aaggagtggt agccgtgtcc tgcgccagca cggcgagagt cgacggctta cgtccttgag    4860
cgcgcatctt acgggcggaa agatcaggaa cataattcag ggtctggatt gcctgcaata    4920
cgcggtcacg cgttgcagga cgcacagatt ctgcattatg catcacccgg gagactgtca    4980
tcatcgacac tcccgccagg cgtgcgacat cctttaatga agccatacccaagccgtttg    5040 ccgtaaaacg ggcactgtag cagaaacaga cgtcactggc gagatccaac gcccatatcac   5100 ctgacacagc aatacaataa aaaataacaa taattcccgg acaattgtcc ccagttccgc   5160
ctctgttctc gccaacgag                                                 5179
```

<210> SEQ ID NO 4
<211> LENGTH: 1248
<212> TYPE: DNA
<213> ORGANISM: Escherichia coli (ATCC9637)
<220> FEATURE:
<221> NAME/KEY: gene
<222> LOCATION: (1)..(1248)
<223> OTHER INFORMATION: cscB

<400> SEQUENCE: 4

```
atggcactga gtattccatt cagaaatgcg tactatcgtt ttgcatccag ttactcattt      60
ctctttttta tttcctggtc gctgtggtgg tcgttatacg ctatttggct gaaaggacat    120
```

-continued

```
ctagggttga cagggacgga attaggtaca ctttattcgg tcaaccagtt taccagcatt      180
ctatttatga tgttctacgg catcgttcag gataaactcg gtctgaagaa accgctcatc      240
tggtgtatga gtttcatcct ggtcttgacc ggaccgttta tgatttacgt ttatgaaccg      300
ttactgcaaa gcaattttc tgtaggtcta attctggggg cgctgttttt tggctggggg      360
tatctggcgg gatgcggttt gcttgatagc ttcaccgaaa aaatggcgcg aaattttcat      420
ttcgaatatg aacagcgcg cgcctgggga tcttttggct atgctattgg cgcgttcttt      480
gccggcatat tttttagtat cagtcccat atcaacttct ggttggtctc gctatttggc      540
gctgtattta tgatgatcaa catgcgtttt aaagataagg atcaccagtg cgtagcggca      600
gatgcgggag gggtaaaaaa agaggatttt atcgcagttt tcaaggatcg aaacttctgg      660
gttttcgtca tatttattgt ggggacgtgg tctttctata acattttga tcaacaactt      720 tttcctgtct tttattcagg tttattcgaa tcacacgatg taggaacgcg cctgtatggt      780
tatctcaact cattccaggt ggtactcgaa gcgctgtgca tggcgattat tccttctctt      840
gtgaatcggg tagggccaaa aaatgcatta cttatcggag ttgtgattat ggcgttgcgt      900
atcctttcct gcgcgctgtt cgttaaccc tggattattt cattagtgaa gttgttacat      960
gccattgagg ttccactttg tgtcatatcc gtcttcaaat acagcgtggc aaactttgat    1020
aagcgcctgt cgtcgacgat ctttctgatt ggttttcaaa ttgccagttc gcttgggatt    1080
gtgctgcttt caacgccgac tgggatactc tttgaccacg caggctacca gacagttttc    1140
ttcgcaattt cgggtattgt ctgcctgatg ttgctatttg gcattttctt cttgagtaaa    1200
aaacgcgagc aaatagttat ggaaacgcct gtaccttcag caatatag                 1248
```

<210> SEQ ID NO 5
<211> LENGTH: 915
<212> TYPE: DNA
<213> ORGANISM: Escherichia coli (ATCC9637)
<220> FEATURE:
<221> NAME/KEY: gene
<222> LOCATION: (1)..(915)
<223> OTHER INFORMATION: cscK

<400> SEQUENCE: 5

```
atgtcagcca agtatgggt tttaggggat gcggtcgtag atctcttgcc agaatcagac       60
gggcgcctac tgccttgtcc tggcggcgcg ccagctaacg ttgcggtggg aatcgccaga      120
ttaggcggaa caagtgggtt tataggtcgg gtgggggatg atcctttgg tgcgttaatg      180 caaagaacgc tgctaactga gggagtcgat atcacgtatc tgaagcaaga tgaatgtcac      240
cggacatcca cggtgcttgt cgatctgaac gatcaagggg aacgttcatt tacgtttatg      300
gtccgcccca gtgccgatct ttttttagag acgacagact tgccctgctg gcgacatggc      360
gaatggttac atctctgttc aattgcgttg tctgccgagc cttcgcgtac cagcgcattt      420
actgcgatga cggcgatccg gcatgccgga ggttttgtca gcttcgatcc taatattcgt      480
gaagatctat ggcaagacga gcatttgctc cgcttgtgtt tgcggcaggc gctacaactg      540
gcggatgtcg tcaagctctc ggaagaagaa tggcgactta cagtggaaa acacagaac       600 gatcaggata tatgcgccct ggcaaaagag tatgagatcg ccatgctgtt ggtgactaaa      660
ggtgcagaag gggtggtggt ctgttatcga ggacaagttc accattttgc tggaatgtct      720
gtgaattgtg tcgatagcac ggggggcgga gatgcgttcg ttgccgggtt actcacaggt      780
ctgtcctcta cggattatc tacagatgag agagaaatgc gacgaattat cgatctcgct      840
caacgttgcg gagcgcttgc agtaacggcg aaaggggcaa tgacagcgct gccatgtcga      900
```

| | |
|---|---:|
| caagaactgg aatag | 915 |

<210> SEQ ID NO 6
<211> LENGTH: 1443
<212> TYPE: DNA
<213> ORGANISM: Escherichia coli (ATCC9637)
<220> FEATURE:
<221> NAME/KEY: gene
<222> LOCATION: (1)..(1443)
<223> OTHER INFORMATION: cscA

<400> SEQUENCE: 6

| | |
|---|---:|
| atgattaaaa tgacgcaatc tcgattgcat gcggcgcaaa acgccctagc aaaacttcat | 60 |
| gagcaccggg gtaacacttt ctatccccat tttcacctcg cgcctcctgc cgggtggatg | 120 |
| aacgatccaa acggcctgat ctggtttaac gatcgttatc acgcgtttta tcaacatcat | 180 |
| ccgatgagcg aacactgggg gccaatgcac tggggacatg ccaccagcga cgatatgatc | 240 |
| cactggcagc atgagcctat tgcgctagcg ccaggagacg ataatgacaa agacgggtgt | 300 |
| ttttcaggta gtgctgtcga tgacaatggt gtcctctcac ttatctacac cggacacgtc | 360 |
| tggctcgatg tgcaggtaa tgacgatgca attcgcgaag tacaatgtct ggctaccagt | 420 |
| cgggatggta ttcatctcga gaaacagggt gtgatcctca ctccaccaga aggaatcatg | 480 |
| cacttccgcg atcctaaagt gtggcgtgaa gccgacacat ggtggatggt agtcggggcg | 540 |
| aaagatccag gcaacacggg gcagatcctg ctttatcgcg gcagttcgtt gcgtgaatgg | 600 |
| accttcgatc gcgtactggc ccacgctgat gcgggtgaaa gctatatgtg gaatgtccg | 660 |
| gacttttca gccttggcga tcagcattat ctgatgtttt ccccgcaggg aatgaatgcc | 720 |
| gagggataca gttaccgaaa tcgctttcaa agtggcgtaa tacccggaat gtggtcgcca | 780 |
| ggacgacttt ttgcacaatc cgggcatttt actgaacttg ataacgggca tgacttttat | 840 |
| gcaccacaaa gcttttttagc gaaggatggt cggcgtattg ttatcggctg gatggatatg | 900 |
| tgggaatcgt caatgccctc aaaacgtgaa ggatgggcag gctgcatgac gctggcgcgc | 960 |
| gagctatcag agagcaatgg caaacttcta caacgcccgg tacacgaagc tgagtcgtta | 1020 |
| cgccagcagc atcaatctgt ctctccccgc acaatcagca taaatatgt tttgcaggaa | 1080 |
| aacgcgcaag cagttgagat tcagttgcag tgggcgctga gaacagtga tgccgaacat | 1140 |
| tacggattac agctcggcac tggaatgcgg ctgtatattg ataaccaatc tgagcgactt | 1200 |
| gttttgtggc ggtattaccc acacgagaat ttagacggct accgtagtat tccctcccg | 1260 |
| cagcgtgaca cgctcgccct aaggatattt atcgatacat catccgtgga agtatttatt | 1320 |
| aacgacgggg aagcggtgat gagtagtcga atctatccgc agccagaaga acgggaactg | 1380 |
| tcgctttatg cctcccacgg agtggctgtg ctgcaacatg gagcactctg gctactgggt | 1440 |
| taa | 1443 |

<210> SEQ ID NO 7
<211> LENGTH: 996
<212> TYPE: DNA
<213> ORGANISM: Escherichia coli (ATCC9637)
<220> FEATURE:
<221> NAME/KEY: gene
<222> LOCATION: (1)..(996)
<223> OTHER INFORMATION: cscR

<400> SEQUENCE: 7

| | |
|---|---:|
| atggcttcat taaaggatgt cgcacgcctg gcgggagtgt cgatgatgac agtctcccgg | 60 |
| gtgatgcata atgcagaatc tgtgcgtcct gcaacgcgtg accgcgtatt gcaggcaatc | 120 |

```
cagaccctga attatgttcc tgatctttcc gcccgtaaga tgcgcgctca aggacgtaag      180
ccgtcgactc tcgccgtgct ggcgcaggac acggctacca ctccttctc tgttgatatt      240 ctgcttgcca ttgagcaaac cgccagcgag ttcggctgga atagtttttt aatcaatatt     300
ttttctgaag atgacgctgc ccgcgcggca cgtcagctgc ttgcccaccg tccggatggc     360
attatctata ctacaatggg gctgcgacat atcacgctgc ctgagtctct gtatggtgaa     420
aatattgtat tggcgaactg tgtggcggat gacccagcgt acccagtta tatccctgat      480 gattacactg cacaatatga atcaacacag catttgctcg cggcgggcta tcgtcaaccg     540
ttatgcttct ggctaccgga aagtgcgttg gcaacagggt atcgtcggca gggatttgag     600
caggcctggc gtgatgctga acgagatctg gctgaggtga acaatttca catggcaaca     660 ggtgatgatc actacaccga tctcgcaagt ttactcaatg cccacttcaa accgggcaaa    720
ccagattttg atgttctgat atgtggtaac gatcgcgcag cctttgtggc ttatcaggtt    780
cttctggcga aggggtacg aatcccgcag gatgtcgccg taatgggctt tgataatctg     840
gttggcgtcg ggcatctgtt tttaccgccg ctgaccacaa ttcagcttcc acatgacatt    900
atcgggcggg aagctgcatt gcatattatt gaaggtcgtg aagggggaag agtgacgcgg    960
atcccttgcc cgctgttgat ccgttgttcc acctga                             996
```

<210> SEQ ID NO 8
<211> LENGTH: 71
<212> TYPE: DNA
<213> ORGANISM: Artificial sequence
<220> FEATURE:
<221> NAME/KEY: gene
<222> LOCATION: (1)..(71)
<223> OTHER INFORMATION: primer for deletion cassette of mak

<400> SEQUENCE: 8

```
gtgcgtatag gtatcgattt aggcggcacc aaaactgaag tgattgcact gttgcagcat      60
tacacgtctt g                                                          71
```

<210> SEQ ID NO 9
<211> LENGTH: 71
<212> TYPE: DNA
<213> ORGANISM: Artificial sequence
<220> FEATURE:
<221> NAME/KEY: gene
<222> LOCATION: (1)..(71)
<223> OTHER INFORMATION: primer for deletion cassette of mak

<400> SEQUENCE: 9

```
ttactcttgt ggccataacc acgcagcgcc gcgtacgccg ctggaatcac cacttaacgg      60
ctgacatggg a                                                          71
```

<210> SEQ ID NO 10
<211> LENGTH: 55
<212> TYPE: DNA
<213> ORGANISM: Artificial sequence
<220> FEATURE:
<221> NAME/KEY: gene
<222> LOCATION: (1)..(55)
<223> OTHER INFORMATION: primer for amplification of cscB to construct
      pAcscBAR

<400> SEQUENCE: 10

```
cgcgatatct agcatatgcc gggtaccgca ctagttgaga agtaaacggc gaagt           55
```

<210> SEQ ID NO 11

```
<211> LENGTH: 46
<212> TYPE: DNA
<213> ORGANISM: Artificial sequence
<220> FEATURE:
<221> NAME/KEY: gene
<222> LOCATION: (1)..(46)
<223> OTHER INFORMATION: primer for amplification of cscB to construct
      pAcscBAR

<400> SEQUENCE: 11
attcggccgg agccctgcag gtgcacgagt acatttgagc gactgt                    46

<210> SEQ ID NO 12
<211> LENGTH: 4520
<212> TYPE: DNA
<213> ORGANISM: Escherichia coli (ATCC9637)
<220> FEATURE:
<221> NAME/KEY: gene
<222> LOCATION: (1)..(4520)
<223> OTHER INFORMATION: polynucleotide containing cscBAR

<400> SEQUENCE: 12
gagccctgca ggtgcacgag tacatttgag cgactgtacc agaacatgaa tgaggcgttt      60
ggattaggcg attattagca gggctaagca ttttactatt attattttcc ggttgaggga     120
tatagagcta tcgacaacaa ccggaaaaag tttacgtcta tattgctgaa ggtacaggcg     180
tttccataac tatttgctcg cgttttttac tcaagaagaa aatgccaaat agcaacatca     240
ggcagacaat acccgaaatt gcgaagaaaa ctgtctggta gcctgcgtgg tcaaagagta     300
tcccagtcgg cgttgaaagc agcacaatcc caagcgaact ggcaatttga aaaccaatca     360
gaaagatcgt cgacgacagg cgcttatcaa agtttgccac gctgtatttg aagacggata     420
tgacacaaag tggaacctca atggcatgta acaacttcac taatgaaata atccaggggt     480
taacgaacag cgcgcaggaa aggatacgca acgccataat cacaactccg ataagtaatg     540
cattttttgg ccctacccga ttcacaaaga aggaataaat cgccatgcac agcgcttcga     600
gtaccacctg gaatgagttg agataaccat acaggcgcgt tcctacatcg tgtgattcga     660
ataaacctga ataaaagaca ggaaaaagtt gttgatcaaa aatgttatag aaagaccacg     720
tccccacaat aaatatgacg aaaacccaga agtttcgatc cttgaaaact gcgataaaat     780 cctcttttttt tacccctccc gcatctgccg ctacgcactg gtgatcctta tctttaaaac     840
gcatgttgat catcataaat acagcgccaa atagcgagac caaccagaag ttgatatggg     900
gactgatact aaaaaatatg ccggcaaaga acgcgccaat agcatagcca aaagatcccc     960
aggcgcgcgc tgttccatat tcgaaatgaa aatttcgcgc cattttttcg gtgaagctat    1020
caagcaaacc gcatcccgcc agatacccca agcaaaaaaa cagcgccccc agaattagac    1080
ctacagaaaa attgctttgc agtaacggtt cataaacgta aatcataaac ggtccggtca    1140
agaccaggat gaaactcata caccagatga gcggtttctt cagaccgagt ttatcctgaa    1200
cgatgccgta gaacatcata aatagaatgc tggtaaactg gttgaccgaa taaagtgtac    1260
ctaattccgt ccctgtcaac cctagatgtc ctttcagcca aatagcgtat aacgaccacc    1320
acagcgacca ggaaataaaa aagagaaatg agtaactgga tgcaaaacga tagtacgcat    1380
ttctgaatgg aatactcagt gccataatta cctgcctgtc gttaaaaaat tcacgtccta    1440
tttagagata agagcgactt cgccgtttac ttctcaacta gtgcggtacc ggcatatgc    1500 tagatatcga ctccctcagt tagcagcgtt ctttgcatta acgcaccaaa aggatcatcc    1560
cccacccgac ctaaaacccc acttgttccg cctaatctgg cgattccac cgcaacgtta    1620 gctggcgcgc cgccaggaca aggcagtagg cgcccgtctg attctggcaa gagatctacg    1680
```

| | |
|---|---|
| accgcatccc ctaaaaccca tactttggct gacatttttt tcccttaaat tcatctgagt | 1740 |
| tacgcatagt gataaacctc tttttcgcaa aatcgtcatg gatttactaa aacatgcata | 1800 |
| ttcgatcaca aaacgtcata gttaacgtta acatttgtga tattcatcgc atttatgaaa | 1860 |
| gtaagggact ttatttttat aaaagttaac gttaacaatt caccaaattt gcttaaccag | 1920 |
| gatgattaaa atgacgcaat ctcgattgca tgcggcgcaa aacgccctag caaaacttca | 1980 |
| tgagcaccgg ggtaacactt tctatcccca ttttcacctc gcgcctcctg ccgggtggat | 2040 |
| gaacgatcca aacggcctga tctggtttaa cgatcgttat cacgcgtttt atcaacatca | 2100 |
| tccgatgagc gaacactggg ggccaatgca ctggggacat gccaccagcg acgatatgat | 2160 |
| ccactggcag catgagccta ttgcgctagc gccaggagac gataatgaca aagacgggtg | 2220 |
| tttttcaggt agtgctgtcg atgacaatgg tgtcctctca cttatctaca ccggacacgt | 2280 |
| ctggctcgat ggtgcaggta atgacgatgc aattcgcgaa gtacaatgtc tggctaccag | 2340 |
| tcgggatggt attcatctcg agaaacaggg tgtgatcctc actccaccag aaggaatcat | 2400 |
| gcacttccgc gatcctaaag tgtggcgtga agccgacaca tggtggatgg tagtcggggc | 2460 |
| gaaagatcca ggcaacacgg ggcagatcct gctttatcgc ggcagttcgt tgcgtgaatg | 2520 |
| gaccttcgat cgcgtactgg cccacgctga tgcgggtgaa agctatatgt gggaatgtcc | 2580 |
| ggactttttc agccttggcg atcagcatta tctgatgttt tccccgcagg gaatgaatgc | 2640 |
| cgagggatac agttaccgaa atcgctttca aagtggcgta ataccggaa tgtggtcgcc | 2700 |
| aggacgactt tttgcacaat ccgggcattt tactgaactt gataacgggc atgactttta | 2760 |
| tgcaccacaa agcttttttag cgaaggatgg tcggcgtatt gttatcggct ggatggatat | 2820 |
| gtgggaatcg tcaatgccct caaaacgtga aggatgggca ggctgcatga cgctggcgcg | 2880 |
| cgagctatca gagagcaatg gcaaacttct acaacgcccg gtacacgaag ctgagtcgtt | 2940 |
| acgccagcag catcaatctg tctctccccg cacaatcagc aataaatatg ttttgcagga | 3000 |
| aaacgcgcaa gcagttgaga ttcagttgca gtgggcgctg aagaacagtg atgccgaaca | 3060 |
| ttacggatta cagctcggca ctggaatgcg gctgtatatt gataaccaat ctgagcgact | 3120 |
| tgttttgtgg cggtattacc cacacgagaa tttagacggc taccgtagta ttccccctccc | 3180 |
| gcagcgtgac acgctcgccc taaggatatt tatcgataca tcatccgtgg aagtatttat | 3240 |
| taacgacggg gaagcggtga tgagtagtcg aatctatccg cagccagaag aacgggaact | 3300 |
| gtcgctttat gcctcccacg gagtggctgt gctgcaacat ggagcactct ggctactggg | 3360 |
| ttaacataat atcaggtgga acaacggatc aacagcgggc aagggatccg cgtcactctt | 3420 |
| cccccttcac gaccttcaat aatatgcaat gcagcttccc gcccgataat gtcatgtgga | 3480 |
| agctgaattg tggtcagcgg cggtaaaaac agatgcccga cgccaaccag attatcaaag | 3540 |
| cccattacgg cgacatcctg cgggattcgt accccccttcg ccagaagaac ctgataagcc | 3600 |
| acaaaggctg cgcgatcgtt accacatatc agaacatcaa aatctggttt gcccggtttg | 3660 |
| aagtgggcat tgagtaaact tgcgagatcg gtgtagtgat catcacctgt tgccatgtga | 3720 |
| aattgtttca cctcagccag atctcgttca gcatcacgcc aggcctgctc aaatccctgc | 3780 |
| cgacgtatacc ctgttgccaa cgcactttcc ggtagccaga agcataacgg ttgacgatag | 3840 |
| cccgccgcga gcaaatgctg tgttgattca tattgtgcag tgtaatcatc agggatataa | 3900 |
| ctgggtaacg ctgggtcatc cgccacacag ttcgccaata caatatttttc accatacaga | 3960 |
| gactcaggca gcgtgatatg tcgcagcccc attgtagtat agataatgcc atccggacgg | 4020 |
| tgggcaagca gctgacgtgc cgcgcgggca gcgtcatctt cagaaaaaat attgattaaa | 4080 |

```
aaactattcc agccgaactc gctggcggtt tgctcaatgg caagcagaat atcaacagag    4140
aaaggagtgg tagccgtgtc ctgcgccagc acggcgagag tcgacggctt acgtccttga    4200
gcgcgcatct tacgggcgga aagatcagga acataattca gggtctggat tgcctgcaat    4260
acgcggtcac gcgttgcagg acgcacagat tctgcattat gcatcacccg ggagactgtc    4320
atcatcgaca ctcccgccag gcgtgcgaca tcctttaatg aagccatacc caagccgttt    4380
gccgtaaaac gggcactgta gcagaaacag acgtcactgg cgagatccaa cgccctatca    4440
cctgacacag caatacaata aaaaataaca ataattcccg gacaattgtc cccagttccg    4500
cctctgttct cgccaacgag                                                4520
```

```
<210> SEQ ID NO 13
<211> LENGTH: 25
<212> TYPE: DNA
<213> ORGANISM: Artificial sequence
<220> FEATURE:
<221> NAME/KEY: gene
<222> LOCATION: (1)..(13)
<223> OTHER INFORMATION: primer for amplification of mak released from
      reference sequence, AP009048 on GeneBank

<400> SEQUENCE: 13
cactgcagtg gggtaaatgc catcg                                            25

<210> SEQ ID NO 14
<211> LENGTH: 25
<212> TYPE: DNA
<213> ORGANISM: Artificial sequence
<220> FEATURE:
<221> NAME/KEY: gene
<222> LOCATION: (1)..(14)
<223> OTHER INFORMATION: primer for amplification of mak released from
      reference sequence, AP009048 on GeneBank

<400> SEQUENCE: 14
aacggccgtc tcggtgctca ttact                                            25

<210> SEQ ID NO 15
<211> LENGTH: 1388
<212> TYPE: DNA
<213> ORGANISM: Escherichia coli K12 W3110
<220> FEATURE:
<221> NAME/KEY: gene
<222> LOCATION: (1)..(1388)
<223> OTHER INFORMATION: polynucleotide containing mak, amplified using
      sequence number 13 and 14

<400> SEQUENCE: 15
```

```
cactgcagtg gggtaaatgc catcgaggct agctgttttt ccatctcttc tgcacgcagc      60
gaaatctcgc ggctaagacg gtaaaccatt aaattttga accacagcat gataatttcc     120
acggccttgt cgttaaattt agcgggcatg ataacgaatt gtcggcgcc ttgcattgcc     180 aatccggttg tccgtctcta cgctattgat attgaaaaaa ataaggagag taccgtgcgt    240
ataggtatcg atttaggcgg caccaaaact gaagtgattg cactgggcga tgcaggggag    300
cagttgtacc gccatcgtct gcccacgccg cgtgatgatt accggcagac tattgaaacg    360
atcgccacgt tggttgatat ggcggagcag gcgacgggc agcgcggaac ggtaggtatg    420
ggcattcctg gctcaatttc gccttacacc ggtgtggtga agaatgccaa ttcaacctgg    480
ctcaacggtc agccattcga taagactta agcgcgaggt tgcagcggga agtgcggctg    540
gcaaatgacg ctaactgtct ggcggtttca gaagcagtag atggcgcggc agcgggagcg    600
```

```
cagacggtat ttgccgtgat tatcggcacg ggatgcggcg cgggcgtggc attcaatggg    660
cgggcgcata tcggcggcaa tggcacggca ggtgagtggg gacacaatcc gctaccgtgg    720
atggacgaag acgaactgcg ttatcgcgag gaagtccctt gttattgcgg taaacaaggt    780
tgtattgaaa cctttatttc gggcacggga ttcgcgatgg attatcgtcg tttgagcgga    840
catgcgctga aaggcagtga aattatccgc ctggttgaag aaagcgatcc ggtagcggaa    900
ctggcattgc gtcgctacga gctgcggctg gcaaaatcgc tggcacatgt cgtgaatatt    960
ctcgatccgg atgtgattgt cctgggggc gggatgagca atgtagaccg tttatatcaa   1020
acggttgggc agttgattaa acaatttgtc ttcggcggcg aatgtgaaac gccggtgcgt   1080
aaggcgaagc acggtgattc cagcggcgta cgcggcgctg cgtggttatg ccacaagag   1140 taaaaaacgt aggcaattgg cgcatcatgc ctgatgcgac gcttgccgcg tcttatcagg   1200
cctacaaaag gtgccagaac cgtaggccgg ataaggcgtt cacgccgcat ccggcaataa   1260
gtgctccgat gcctgatgcg acgcttgccg cgtcttatca ggcctgcaaa atgtgccaga   1320
accgcgtagg gcggataagg cgttcacgcc gcatccggca ataagtaatg agcaccgaga   1380
cggccgtt                                                            1388
```

<210> SEQ ID NO 16
<211> LENGTH: 5887
<212> TYPE: DNA
<213> ORGANISM: Escherichia coli (ATCC9637) and K12 W3110
<220> FEATURE:
<221> NAME/KEY: gene
<222> LOCATION: (1)..(5887)
<223> OTHER INFORMATION: polynucleotide containing cscBAR-mak

<400> SEQUENCE: 16

```
tctcggtgct cattacttat tgccggatgc ggcgtgaacg cctatccgc cctacgcggt     60 tctggcacat tttgcaggcc tgataagacg cggcaagcgt cgcatcaggc atcggagcac    120
ttattgccgg atgcggcgtg aacgcctat ccggcctacg gttctggcac ctttttgtagg   180 cctgataaga cgcggcaagc gtcgcatcag catgatgcg ccaattgcct acgtttttta    240
ctcttgtggc cataaccacg cagcgccgcg tacgccgctg gaatcaccgt gcttcgcctt    300
acgcaccggc gtttcacatt cgccgccgaa gacaaattgt ttaatcaact gcccaaccgt    360
ttgatataaa cggtctacat tgctcatccc gccccccagg acaatcacat ccggatcgag    420
aatattcacg acatgtgcca gcgattttgc cagccgcagc tcgtagcgac gcaatgccag    480
ttccgctacc ggatcgcttt cttcaaccag gcggataatt tcactgcctt tcagcgcatg    540
tccgctcaaa cgacgataat ccatcgcgaa tcccgtgccc gaaataaagg tttcaataca    600
accttgttta ccgcaataac aagggacttc ctcgcgataa cgcagttcgt cttcgtccat    660
ccacggtagc ggattgtgtc cccactcacc tgccgtgcca ttgccgccga tatgcgcccg    720
cccattgaat gccacgcccg cgccgcatcc cgtgccgata tcacggcaa ataccgtctg    780 cgctcccgct gccgcgccat ctactgcttc tgaaaccgcc agacagttag cgtcatttgc    840
cagccgcact tcccgctgca acctcgcgct taagtcttta tcgaatggct gaccgttgag    900
ccaggttgaa ttggcattct tcaccacacc ggtgtaaggc gaaattgagc caggaatgcc    960
catacctacc gttccgcgct gccccgtcgc ctgctccgcc atatcaacca acgtggcgat   1020
cgtttcaata gtctgccggt aatcatcacg cggcgtgggc agacgatggc ggtacaactg   1080 ctccccctgca tcgcccagtg caatcacttc agttttggtg ccgcctaaat cgataccat   1140 acgcacggta ctctccttat tttttcaat atcaatagcg tagagacgga caaccggatt   1200
```

```
ggcaatgcaa ggccgccgac aattcgttat catgcccgct aaatttaacg acaaggccgt      1260
ggaaattatc atgctgtggt tcaaaaattt aatggtttac cgtcttagcc gcgagatttc      1320
gctgcgtgca gaagagatgg aaaaacagct agcctcgatg gcatttaccc cactgcaggt      1380
gcacgagtac atttgagcga ctgtaccaga acatgaatga ggcgtttgga ttaggcgatt      1440
attagcaggg ctaagcattt tactattatt atttccggt tgagggatat agagctatcg       1500
acaacaaccg gaaaaagttt acgtctatat tgctgaaggt acaggcgttt ccataactat       1560
ttgctcgcgt tttttactca agaagaaaat gccaaatagc aacatcaggc agacaatacc      1620
cgaaattgcg aagaaaactg tctggtagcc tgcgtggtca aagagtatcc cagtcggcgt      1680
tgaaagcagc acaatcccaa gcgaactggc aatttgaaaa ccaatcagaa agatcgtcga      1740
cgacaggcgc ttatcaaagt ttgccacgct gtatttgaag acggatatga cacaaagtgg      1800
aacctcaatg gcatgtaaca acttcactaa tgaaataatc caggggttaa cgaacagcgc      1860
gcaggaaagg atacgcaacg ccataatcac aactccgata agtaatgcat tttttggccc      1920
tacccgattc acaaagaaag gaataatcgc catgcacagc gcttcgagta ccacctggaa      1980
tgagttgaga taaccataca ggcgcgttcc tacatcgtgt gattcgaata aacctgaata      2040
aaagacagga aaagttgtt gatcaaaaat gttatagaaa gaccacgtcc ccacaataaa       2100
tatgacgaaa acccagaagt ttcgatcctt gaaaactgcg ataaaatcct cttttttac       2160 ccctcccgca tctgccgcta cgcactggtg atccttatct ttaaaacgca tgttgatcat      2220
cataaataca gcgccaaata gcgagaccaa ccagaagttg atatggggac tgatactaaa      2280
aaatatgccg gcaaagaacg cgccaatagc atagccaaaa gatccccagg cgcgcgctgt      2340
tccatattcg aaatgaaaat ttcgcgccat ttttcggtg aagctatcaa gcaaaccgca       2400
tcccgccaga tacccccagc caaaaaacag cgccccaga attagaccta cagaaaaatt       2460
gctttgcagt aacggttcat aaacgtaaat cataaacggt ccggtcaaga ccaggatgaa      2520
actcatacac cagatgagcg gtttcttcag accgagtta tcctgaacga tgccgtagaa       2580
catcataaat agaatgctgg taaactggtt gaccgaataa agtgtaccta attccgtccc      2640
tgtcaaccct agatgtcctt tcagccaaat agcgtataac gaccaccaca gcgaccagga      2700
aataaaaaag agaaatgagt aactggatgc aaaacgatag tacgcatttc tgaatggaat      2760
actcagtgcc ataattacct gcctgtcgtt aaaaaattca cgtcctattt agagataaga      2820
gcgacttcgc cgtttacttc tcaactagtg cggtacccgg catatgctag atatcgactc      2880
cctcagttag cagcgttctt tgcattaacg caccaaaagg atcatccccc acccgaccta      2940
taaacccact tgttccgcct aatctggcga ttcccaccgc aacgttagct ggcgcgccgc      3000
caggacaagg cagtaggcgc ccgtctgatt ctggcaagag atctacgacc gcatccccta      3060
aaacccatac tttggctgac attttttttcc cttaaattca tctgagttac gcatagtgat      3120
aaacctcttt ttcgcaaaat cgtcatggat ttactaaaac atgcatattc gatcacaaaa      3180
cgtcatagtt aacgttaaca tttgtgatat tcatcgcatt tatgaaagta agggacttta      3240
tttttataaa agttaacgtt aacaattcac caaatttgct taaccaggat gattaaaatg      3300
acgcaatctc gattgcatgc ggcgcaaaac gccctagcaa aacttcatga gcaccggggt      3360
aacactttct atccccattt tcacctcgcg cctcctgccg ggtggatgaa cgatccaaac      3420
ggcctgatct ggttttaacga tcgttatcac gcgtttttatc aacatcatcc gatgagcgaa      3480
cactgggggc caatgcactg gggacatgcc accagcgacg atatgatcca ctggcagcat      3540
gagcctattg cgctagcgcc aggagacgat aatgacaaag acgggtgttt ttcaggtagt      3600
```

```
gctgtcgatg acaatggtgt cctctcactt atctacaccg gacacgtctg gctcgatggt    3660
gcaggtaatg acgatgcaat tcgcgaagta caatgtctgg ctaccagtcg ggatggtatt    3720
catctcgaga aacagggtgt gatcctcact ccaccagaag gaatcatgca cttccgcgat    3780
cctaaagtgt ggcgtgaagc cgacacatgg tggatggtag tcggggcgaa agatccaggc    3840
aacacggggc agatcctgct ttatcgcggc agttcgttgc gtgaatggac cttcgatcgc    3900
gtactggccc acgctgatgc gggtgaaagc tatatgtggg aatgtccgga cttttcagc     3960
cttggcgatc agcattatct gatgttttcc ccgcagggaa tgaatgccga gggatacagt    4020
taccgaaatc gctttcaaag tggcgtaata cccggaatgt ggtcgccagg acgacttttt    4080
gcacaatccg ggcattttac tgaacttgat aacgggcatg acttttatgc accacaaagc    4140
tttttagcga aggatggtcg gcgtattgtt atcggctgga tggatatgtg gaatcgtca     4200
atgccctcaa aacgtgaagg atgggcaggc tgcatgacgc tggcgcgcga gctatcagag    4260
agcaatggca aacttctaca acgcccggta cacgaagctg agtcgttacg ccagcagcat    4320
caatctgtct ctcccgcac aatcagcaat aaatatgttt tgcaggaaaa cgcgcaagca     4380
gttgagattc agttgcagtg ggcgctgaag aacagtgatg ccgaacatta cggattacag    4440
ctcggcactg gaatgcggct gtatattgat aaccaatctg agcgacttgt tttgtggcgg    4500
tattacccac acgagaattt agacggctac cgtagtattc ccctcccgca gcgtgacacg    4560
ctcgccctaa ggatatttat cgatacatca tccgtggaag tatttattaa cgacggggaa    4620
gcggtgatga gtagtcgaat ctatccgcag ccagaagaac gggaactgtc gctttatgcc    4680
tcccacggag tggctgtgct gcaacatgga gcactctggc tactgggtta acataatatc    4740
aggtggaaca acggatcaac agcgggcaag ggatccgcgt cactcttccc ccttcacgac    4800
cttcaataat atgcaatgca gcttcccgcc cgataatgtc atgtggaagc tgaattgtgg    4860
tcagcggcgg taaaaacaga tgcccgacgc caaccagatt atcaaagccc attacgcga     4920
catcctgcgg gattcgtacc cccttcgcca gaagaacctg ataagccaca aaggctgcgc    4980
gatcgttacc acatatcaga acatcaaat ctggtttgcc cggtttgaag tgggcattga     5040
gtaaacttgc gagatcggtg tagtgatcat cacctgttgc catgtgaaat tgtttcacct    5100
cagccagatc tcgttcagca tcacgccagg cctgctcaaa tccctgccga cgataccctg    5160
ttgccaacgc actttccggt agccagaagc ataacggttg acgatagccc gccgcgagca    5220
aatgctgtgt tgattcatat tgtgcagtgt aatcatcagg gatataactg ggtaacgctg    5280
ggtcatccgc cacacagttc gccaatacaa tattttcacc atacagagac tcaggcagcg    5340
tgatatgtcg cagccccatt gtagtataga taatgccatc cggacggtgg gcaagcagct    5400
gacgtgccgc gcgggcagcg tcatcttcag aaaaaatatt gattaaaaa ctattccagc     5460
cgaactcgct ggcggtttgc tcaatggcaa gcagaatatc aacagagaaa ggagtggtag    5520
ccgtgtcctg cgccagcacg gcgagagtcg acggcttacg tccttgagcg cgcatcttac    5580
gggcggaaag atcaggaaca taattcaggg tctggattgc ctgcaatacg cggtcacgcg    5640
ttgcaggacg cacagattct gcattatgca tcacccggga gactgtcatc atcgacactc    5700
ccgccaggcg tgcgacatcc tttaatgaag ccatacccaa gccgtttgcc gtaaaacggg    5760
cactgtagca gaaacagacg tcactggcga gatccaacgc cctatcacct gacacagcaa    5820
tacaataaaa aataacaata attcccggac aattgtcccc agttccgcct ctgttctcgc    5880
caacgag                                                              5887
```

<210> SEQ ID NO 17

```
<211> LENGTH: 996
<212> TYPE: DNA
<213> ORGANISM: Escherichia coli (ATCC9637)
<220> FEATURE:
<221> NAME/KEY: gene
<222> LOCATION: (1)..(996)
<223> OTHER INFORMATION: cscR mutated tyrosine on 388th amino acid

<400> SEQUENCE: 17
atggcttcat taaaggatgt cgcacgcctg gcgggagtgt cgatgatgac agtctcccgg      60
gtgatgcata atgcagaatc tgtgcgtcct gcaacgcgtg accgcgtatt gcaggcaatc     120
cagaccctga attatgttcc tgatctttcc gcccgtaaga tgcgcgctca aggacgtaag     180
ccgtcgactc tcgccgtgct ggcgcaggac acggctacca ctcctttctc tgttgatatt     240
ctgcttgcca ttgagcaaac cgccagcgag ttcggctgga atagttttt aatcaatatt     300 ttttctgaag atgacgctgc ccgcgcggca cgtcagctgc ttgcccaccg tccggatggc     360
attatctata ctacaatggg gctgcgatat atcacgctgc ctgagtctct gtatggtgaa     420
aatattgtat tggcgaactg tgtggcggat gacccagcgt acccagttat atccctgat    480 gattacactg cacaatatga atcaacacag catttgctcg cggcgggcta tcgtcaaccg     540
ttatgcttct ggctaccgga agtgcgttg gcaacagggt atcgtcggca gggatttgag     600
caggcctggc gtgatgctga acgagatctg gctgaggtga acaatttca catggcaaca     660 ggtgatgatc actacaccga tctcgcaagt ttactcaatg cccacttcaa accgggcaaa     720
ccagattttg atgttctgat atgtggtaac gatcgcgcag cctttgtggc ttatcaggtt     780
cttctggcga agggggtacg aatcccgcag gatgtcgccg taatgggctt tgataatctg     840
gttggcgtcg gcatctgtt tttaccgccg ctgaccacaa ttcagcttcc acatgacatt     900
atcgggcggg aagctgcatt gcatattatt gaaggtcgtg aaggggaag agtgacgcgg     960 atcccttgcc cgctgttgat ccgttgttcc acctga                              996

<210> SEQ ID NO 18
<211> LENGTH: 9129
<212> TYPE: DNA
<213> ORGANISM: Escherichia coli (ATCC9637) and K12 W3110
<220> FEATURE:
<221> NAME/KEY: gene
<222> LOCATION: (1)..(9129)
<223> OTHER INFORMATION: pAcscBAR'-mak

<400> SEQUENCE: 18
tatggcaatg aaagacggtg agctggtgat atgggatagt gttcaccctt gttacaccgt      60
tttccatgag caaactgaaa cgttttcatc gctctggagt gaataccacg acgatttccg     120
gcagtttcta cacatatatt cgcaagatgt ggcgtgttac ggtgaaaacc tggcctattt     180
ccctaaaggg tttattgaga atatgttttt cgtctcagcc aatccctggg tgagtttcac     240
cagttttgat ttaaacgtgg ccaatatgga caacttcttc gccccgtttt tcaccatggg     300
caaatattat acgcaaggcg acaaggtgct gatgccgctg gcgattcagg ttcatcatgc     360
cgtctgtgat ggcttccatg tcggcagaat gcttaatgaa ttacaacagt actgcgatga     420
gtggcagggc ggggcgtaat tttttaagg cagttattgg tgcccttaaa cgcctggtgc    480
tacgcctgaa taagtgataa taagcggatg aatggcagaa attcgaaagc aaattcgacc     540
cggtcgtcgg ttcagggcag ggtcgttaaa tagccgctta tgtctattgc tggtttaccg     600
gtttattgac taccggaagc agtgtgaccg tgtgcttctc aaatgcctga ggccagtttg     660
ctcaggctct ccccgtggag gtaataattg acgatatgat catttattct gcctcccaga     720
```

```
gcctgataaa aacggttagc gcttcgttaa tacagatgta ggtgttccac agggtagcca    780
gcagcatcct gcgatgcaga tccggaacat aatggtgcag ggcgcttgtt tcggcgtggg    840
tatggtggca ggccccgtgg ccgggggact gttgggcgct gccggcacct gtcctacgag    900
ttgcatgata aagaagacag tcataagtgc ggcgacgata gtcatgcccc cgcccaccg     960 gaaggagcta ccggacagcg gtgcggactg ttgtaactca gaataagaaa tgaggccgct   1020
catggcgttg actctcagtc atagtatcgt ggtatcaccg gttggttcca ctctctgttg   1080
cgggcaactt cagcagcacg taggggactt ccgcgtttcc agactttacg aaacacggaa   1140
accgaagacc attcatgttg ttgctcaggt cgcagacgtt ttgcagcagc agtcgcttca   1200
cgttcgctcg cgtatcggtg attcattctg ctaaccagta aggcaacccc gccagcctag   1260
ccgggtcctc aacgacagga gcacgatcat gcgcacccgt ggccaggacc caacgctgcc   1320
cgagatgcgc cgcgtgcggc tgctggagat ggcggacgcg atggatatgt tctgccaagg   1380
gttggtttgc gcattcacag ttctccgcaa gaattgattg gctccaattc ttggagtggt   1440
gaatccgtta gcgaggtgcc gccggcttcc attcaggtcg aggtggcccg gctccatgca   1500
ccgcgacgca acgcggggag gcagacaagg tataggggcgg cgcctacaat ccatgccaac   1560
ccgttccatg tgctcgccga ggcggcataa atcgccgtga cgatcagcgg tccagtgatc   1620
gaagttaggc tggtaagagc cgcgagcgat ccttgaagct gtccctgatg gtcgtcatct   1680
acctgcctgg acagcatggc ctgcaacgcg ggcatcccga tgccgccgga agcgagaaga   1740
atcataatgg ggaaggccat ccagcctcgc gtcgcgaacg ccagcaagac gtagcccagc   1800
gcgtcggccg tctcggtgct cattacttat tgccggatgc ggcgtgaacg ccttatccgc   1860
cctacgcggt tctggcacat tttgcaggcc tgataagacg cggcaagcgt cgcatcaggc   1920
atcggagcac ttattgccgg atgcggcgtg aacgccttat ccggcctacg gttctggcac   1980
cttttgtagg cctgataaga gcggcaagc gtcgcatcag gcatgatgcg ccaattgcct   2040
acgtttttta ctcttgtggc cataaccacg cagcgccgcg tacgccgctg gaatcaccgt   2100
gcttcgcctt acgcaccggc gtttcacatt cgccgccgaa gacaaattgt ttaatcaact   2160
gcccaaccgt ttgatataaa cggtctacat tgctcatccc gccccccagg acaatcacat   2220
ccggatcgag aatattcacg acatgtgcca gcgattttgc cagccgcagc tcgtagcgac   2280
gcaatgccag ttccgctacc ggatcgcttt cttcaaccag gcggataatt tcactgcctt   2340
tcagcgcatg tccgctcaaa cgacgataat ccatcgcgaa tcccgtgccc gaaataaagg   2400
tttcaataca accttgttta ccgcaataac aagggacttc ctcgcgataa cgcagttcgt   2460
cttcgtccat ccacggtagc ggattgtgtc cccactcacc tgccgtgcca ttgccgccga   2520
tatgcgcccg cccattgaat gccacgcccg cgccgcatcc cgtgccgata tcacggcaa    2580 ataccgtctg cgctcccgct gccgcgccat ctactgcttc tgaaaccgcc agacagttag   2640
cgtcatttgc cagccgcact tcccgctgca acctcgcgct taagtctttta tcgaatggct   2700 gaccgttgag ccaggttgaa ttggcattct tcaccacacc ggtgtaaggc gaaattgagc   2760
caggaatgcc catacctacc gttccgcgct gccccgtcgc ctgctccgcc atatcaacca   2820
acgtggcgat cgtttcaata gtctgccggt aatcatcacg cggcgtgggc agacgatggc   2880
ggtacaactg ctcccctgca tcgcccagtg caatcacttc agttttggtg ccgcctaaat   2940
cgatacctat acgcacggta ctctccttat ttttttcaat atcaatagcg tagagacgga   3000
caaccggatt ggcaatgcaa ggccgccgac aattcgttat catgcccgct aaatttaacg   3060
acaaggccgt ggaaattatc atgctgtggt tcaaaaattt aatggtttac cgtcttagcc   3120
```

```
gcgagatttc gctgcgtgca gaagagatgg aaaaacagct agcctcgatg gcatttaccc   3180
cactgcaggt gcacgagtac atttgagcga ctgtaccaga acatgaatga ggcgtttgga   3240
ttaggcgatt attagcaggg ctaagcattt tactattatt attttccggt tgagggatat   3300
agagctatcg acaacaaccg gaaaaagttt acgtctatat tgctgaaggt acaggcgttt   3360
ccataactat ttgctcgcgt tttttactca agaagaaaat gccaaatagc aacatcaggc   3420
agacaatacc cgaaattgcg aagaaaactg tctggtagcc tgcgtggtca aagagtatcc   3480
cagtcggcgt tgaaagcagc acaatcccaa gcgaactggc aatttgaaaa ccaatcagaa   3540
agatcgtcga cgacaggcgc ttatcaaagt ttgccacgct gtatttgaag acggatatga   3600
cacaaagtgg aacctcaatg gcatgtaaca acttcactaa tgaaataatc cagggggttaa   3660 cgaacagcgc gcaggaaagg atacgcaacg ccataatcac aactccgata agtaatgcat   3720
tttttggccc tacccgattc acaaagaaag gaataatcgc catgcacagc gcttcgagta   3780
ccacctggaa tgagttgaga taaccataca ggcgcgttcc tacatcgtgt gattcgaata   3840
aacctgaata aaagacagga aaagttgtt gatcaaaaat gttatagaaa gaccacgtcc   3900
ccacaataaa tatgacgaaa acccagaagt ttcgatcctt gaaaactgcg ataaaatcct   3960 cttttttac ccctcccgca tctgccgcta cgcactggtg atccttatct ttaaaacgca   4020
tgttgatcat cataaataca gcgccaaata gcgagaccaa ccagaagttg atatggggac   4080
tgatactaaa aaatatgccg gcaaagaacg cgccaatagc atagccaaaa gatccccagg   4140
cgcgcgctgt tccatattcg aaatgaaaat ttcgcgccat tttttcggtg aagctatcaa   4200
gcaaaccgca tcccgccaga tacccccagc caaaaaacag cgcccccaga attagaccta   4260
cagaaaaatt gctttgcagt aacggttcat aaacgtaaat cataaacggt ccggtcaaga   4320
ccaggatgaa actcatacac cagatgagcg gtttcttcag accgagttta tcctgaacga   4380
tgccgtagaa catcataaat agaatgctgg taaactggtt gaccgaataa agtgtaccta   4440
attccgtccc tgtcaaccct agatgtcctt tcagccaaat agcgtataac gaccaccaca   4500
gcgaccagga aataaaaaag agaaatgagt aactggatgc aaaacgatag tacgcatttc   4560
tgaatggaat actcagtgcc ataattacct gcctgtcgtt aaaaaattca cgtcctattt   4620
agagataaga gcgacttcgc cgtttacttc tcaactagtg cggtacccgg catatgctag   4680
atatcgactc cctcagttag cagcgttctt tgcattaacg caccaaaagg atcatccccc   4740
acccgaccta taaacccact tgttccgcct aatctggcga ttcccaccgc aacgttagct   4800
ggcgcgccgc caggacaagg cagtaggcgc ccgtctgatt ctggcaagag atctacgacc   4860
gcatccccta aaacccatac tttggctgac attttttttcc cttaaattca tctgagttac   4920
gcatagtgat aaacctcttt ttcgcaaaat cgtcatggat ttactaaaac atgcatattc   4980
gatcacaaaa cgtcatagtt aacgttaaca tttgtgatat tcatcgcatt tatgaaagta   5040
agggacttta ttttataaa agttaacgtt aacaattcac caaatttgct taaccaggat   5100
gattaaaatg acgcaatctc gattgcatgc ggcgcaaaac gccctagcaa aacttcatga   5160
gcaccggggt aacactttct atccccattt tcacctcgcg cctcctgccg ggtggatgaa   5220
cgatccaaac ggcctgatct ggtttaacga tcgttatcac gcgttttatc aacatcatcc   5280
gatgagcgaa cactggggc caatgcactg gggacatgcc accagcgacg atatgatcca   5340
ctggcagcat gagcctattg cgctagcgcc aggagacgat aatgacaaag acgggtgttt   5400
ttcaggtagt gctgtcgatg acaatggtgt cctctcactt atctacaccg gacacgtctg   5460
gctcgatggt gcaggtaatg acgatgcaat tcgcgaagta caatgtctgg ctaccagtcg   5520
```

```
ggatggtatt catctcgaga aacagggtgt gatcctcact ccaccagaag gaatcatgca   5580
cttccgcgat cctaaagtgt ggcgtgaagc cgacacatgg tggatggtag tcggggcgaa   5640
agatccaggc aacacggggc agatcctgct ttatcgcggc agttcgttgc gtgaatggac   5700
cttcgatcgc gtactggccc acgctgatgc gggtgaaagc tatatgtggg aatgtccgga   5760 cttttttcagc cttggcgatc agcattatct gatgttttcc ccgcagggaa tgaatgccga   5820
gggatacagt taccgaaatc gctttcaaag tggcgtaata cccggaatgt ggtcgccagg   5880
acgacttttt gcacaatccg ggcattttac tgaacttgat aacgggcatg acttttatgc   5940
accacaaagc tttttagcga aggatggtcg gcgtattgtt atcggctgga tggatatgtg   6000
ggaatcgtca atgccctcaa acgtgaagg atgggcaggc tgcatgacgc tggcgcgcga   6060
gctatcagag agcaatggca aacttctaca acgcccggta cacgaagctg agtcgttacg   6120
ccagcagcat caatctgtct ctccccgcac aatcagcaat aaatatgttt tgcaggaaaa   6180
cgcgcaagca gttgagattc agttgcagtg ggcgctgaag aacagtgatg ccgaacatta   6240
cggattacag ctcggcactg gaatgcggct gtatattgat aaccaatctg agcgacttgt   6300
tttgtggcgg tattacccac acgagaattt agacggctac cgtagtattc ccctcccgca   6360
gcgtgacacg ctcgccctaa ggatatttat cgatacatca tccgtggaag tatttattaa   6420
cgacggggaa gcggtgatga gtagtcgaat ctatccgcag ccagaagaac gggaactgtc   6480
gctttatgcc tcccacggag tggctgtgct gcaacatgga gcactctggc tactgggtta   6540
acataatatc aggtggaaca acggatcaac agcgggcaag ggatccgcgt cactcttccc   6600
ccttcacgac cttcaataat atgcaatgca gcttcccgcc cgataatgtc atgtggaagc   6660
tgaattgtgg tcagcggcgg taaaaacaga tgcccgacgc caaccagatt atcaaagccc   6720
attacggcga catcctgcgg gattcgtacc cccttcgcca gaagaacctg ataagccaca   6780
aaggctgcgc gatcgttacc acatatcaga acatcaaaat ctggtttgcc cggtttgaag   6840
tgggcattga gtaaacttgc gagatcggtg tagtgatcat cacctgttgc catgtgaaat   6900
tgtttcacct cagccagatc tcgttcagca tcacgccagg cctgctcaaa tccctgccga   6960 cgatacccctg ttgccaacgc actttccggt agccagaagc ataacggttg acgatagccc   7020
gccgcgagca aatgctgtgt tgattcatat tgtgcagtgt aatcatcagg gatataactg   7080
ggtaacgctg ggtcatccgc cacacagttc gccaatacaa tattttcacc atacagagac   7140
tcaggcagcg tgatatatcg cagccccatt gtagtataga taatgccatc cggacggtgg   7200
gcaagcagct gacgtgccgc gcgggcagcg tcatcttcag aaaaaatatt gattaaaaaa   7260
ctattccagc cgaactcgct ggcggtttgc tcaatggcaa gcagaatatc aacagagaaa   7320
ggagtggtag ccgtgtcctg cgccagcacg gcgagagtcg acggcttacg tccttgagcg   7380
cgcatcttac gggcggaaag atcaggaaca taattcaggg tctggattgc ctgcaatacg   7440
cggtcacgcg ttgcaggacg cacagattct gcattatgca tcacccggga gactgtcatc   7500
atcgacactc ccgccaggcg tgcgacatcc tttaatgaag ccatacccaa gccgtttgcc   7560
gtaaaacggg cactgtagca gaaacagacg tcactggcga gatccaacgc cctatcacct   7620
gacacagcaa tacaataaaa aataacaata attcccggac aattgtcccc agttccgcct   7680
ctgttctcgc caacgagtct agaaatattt tatctgatta ataagatgat cttcttgaga   7740
tcgttttggt ctgcgcgtaa tctcttgctc tgaaaacgaa aaaccgcct tgcagggcgg   7800 tttttcgaag gttctctgag ctaccaactc tttgaaccga ggtaactggc ttggaggagc   7860
gcagtcacca aaacttgtcc tttcagttta gccttaaccg gcgcatgact tcaagactaa   7920
```

-continued

```
ctcctctaaa tcaattacca gtggctgctg ccagtggtgc ttttgcatgt ctttccgggt    7980
tggactcaag acgatagtta ccggataagg cgcagcggtc ggactgaacg gggggttcgt    8040
gcatacagtc cagcttggag cgaactgcct acccggaact gagtgtcagg cgtggaatga    8100
gacaaacgcg gccataacag cggaatgaca ccggtaaacc gaaaggcagg aacaggagag    8160
cgcacgaggg agccgccagg gggaaacgcc tggtatcttt atagtcctgt cgggtttcgc    8220
caccactgat ttgagcgtca gatttcgtga tgcttgtcag gggggcggag cctatggaaa    8280
aacggctttg ccgcggccct ctcacttccc tgttaagtat cttcctggca tcttccagga    8340
aatctccgcc ccgttcgtaa gccatttccg ctcgccgcag tcgaacgacc gagcgtagcg    8400
agtcagtgag cgaggaagcg gaatatatcc tgtatcacat attctgctga cgcaccggtg    8460 cagcctttt  tctcctgcca catgaagcac ttcactgaca ccctcatcag tgccaacata    8520
gtaagccagt atacactccg ctagcgctga tgtccggcgg tgcttttgcc gttacgcacc    8580
accccgtcag tagctgaaca ggagggacag ctgatagaaa cagaagccac tggagcacct    8640
caaaaacacc atcatacact aaatcagtaa gttggcagca tcacccgacg cactttgcgc    8700
cgaataaata cctgtgacgg aagatcactt cgcagaataa ataaatcctg gtgtccctgt    8760
tgataccggg aagccctggg ccaactttg  gcgaaaatga gacgttgatc ggcacgtaag    8820
aggttccaac tttcaccata atgaaataag atcactaccg ggcgtatttt ttgagttatc    8880
gagattttca ggagctaagg aagctaaaat ggagaaaaaa atcactggat ataccaccgt    8940
tgatatatcc caatggcatc gtaaagaaca ttttgaggca tttcagtcag ttgctcaatg    9000
tacctataac cagaccgttc agctggatat tacggccttt ttaaagaccg taaagaaaaa    9060
taagcacaag ttttatccgg cctttattca cattcttgcc cgcctgatga atgctcatcc    9120
ggaattccg                                                            9129
```